US006527744B1

(12) United States Patent
Kriesel et al.

(10) Patent No.: US 6,527,744 B1
(45) Date of Patent: Mar. 4, 2003

(54) FLUID DELIVERY DEVICE WITH LIGHT ACTIVATED ENERGY SOURCE

(75) Inventors: Marshall S. Kriesel, St. Paul; Thomas N. Thompson, Richfield, both of MN (US)

(73) Assignee: Science Incorporated, Bloomington, MN (US)

( * ) Notice: Subject to any disclaimer, the term of this patent is extended or adjusted under 35 U.S.C. 154(b) by 70 days.

(21) Appl. No.: 09/607,519

(22) Filed: Jun. 28, 2000

Related U.S. Application Data

(60) Continuation-in-part of application No. 09/387,447, filed on Sep. 1, 1999, which is a division of application No. 08/919,147, filed on Aug. 27, 1997, now Pat. No. 5,961,492.

(51) Int. Cl.[7] .............................................. A61M 37/00
(52) U.S. Cl. .................................... 604/132; 604/891.1
(58) Field of Search ................................ 600/310, 342, 600/476, 478; 604/132, 65, 67, 151, 153, 185, 890.1, 891.1, 131; 128/DIG. 12

(56) References Cited

U.S. PATENT DOCUMENTS

| | | | | |
|---|---|---|---|---|
| 4,732,930 A | | 3/1988 | Tanaka et al. .............. 524/742 |
| 5,263,323 A | | 11/1993 | Maus et al. ................... 60/528 |
| 5,368,570 A | * | 11/1994 | Thompson et al. ......... 604/132 |
| 5,403,893 A | * | 4/1995 | Tanaka et al. .............. 523/105 |
| RE35,068 E | | 10/1995 | Tanaka et al. .............. 523/300 |
| 5,505,706 A | * | 4/1996 | Maus et al. .............. 604/890.1 |
| 5,616,127 A | | 4/1997 | Tanaka et al. .............. 604/118 |
| 5,961,492 A | * | 10/1999 | Kriesel et al. .............. 604/132 |

FOREIGN PATENT DOCUMENTS

| WO | WO96/02276 | 2/1996 |
|---|---|---|
| WO | WO96/40032 | 12/1996 |

OTHER PUBLICATIONS

Physical Review Letters, vol. 45, No. 20 Phase Transitions in Ionic Gels.
Physical Review Letters, vol. 40, No. 12 Collapse of Gels and the Critical Endpoint.

\* cited by examiner

*Primary Examiner*—Anhtuan T. Nguyen
(74) *Attorney, Agent, or Firm*—Schwegman, Lundberg, Woessner & Kluth, P.A.

(57) ABSTRACT

A fluid delivery apparatus for infusing medicinal fluids into a patient which is of a compact, low profile, laminate construction. The apparatus embodies a novel light activated expanding polymer material which uniquely functions as an internal energy source for expelling the medicinal fluids from the device. The light polymer mass is activated by a novel light source in a manner to controllably expel fluid from the device. Further, the light actuated polymer can be specifically tailored to provide precise, predictable protocol delivery of the medicinal agent stored within the reservoir of the device. In one form of the invention, the fluid delivery apparatus is implantable within the patient's body.

36 Claims, 35 Drawing Sheets

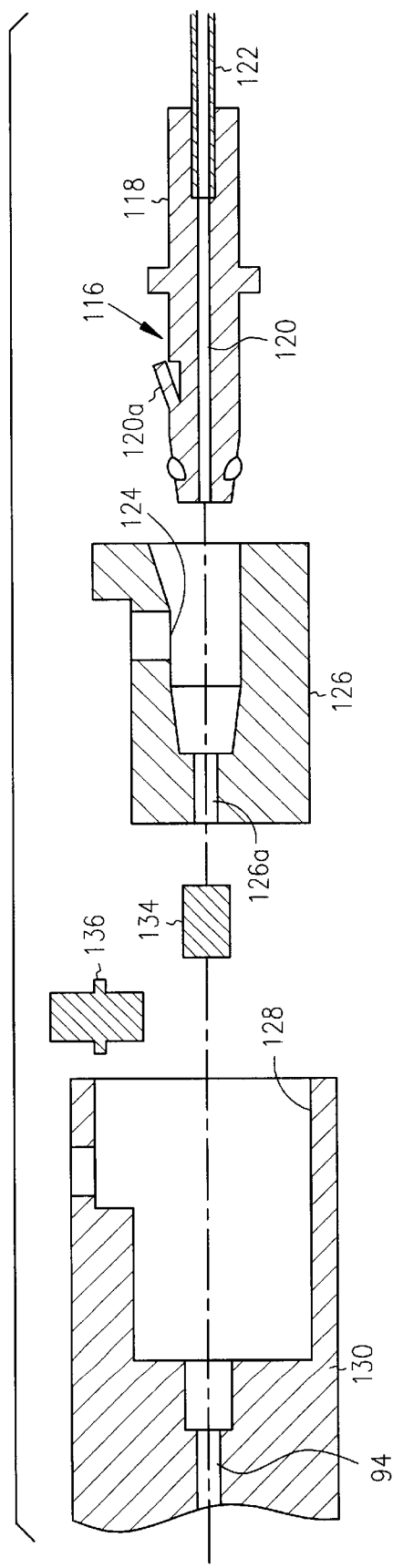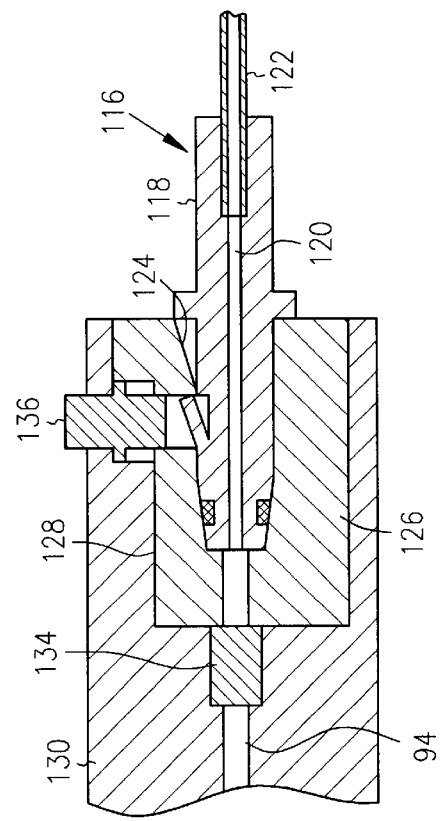
FIG. 14
FIG. 14A

FLUID DELIVERY DEVICE WITH LIGHT ACTIVATED ENERGY SOURCE

This is a Continuation-In-Part of co-pending application Ser. No. 09/387,447 filed Sep. 1, 1999 which is a Divisional application of application Ser. No. 08/919,147 filed Aug. 27, 1997, now U.S. Pat. No. 5,961,492.

BACKGROUND OF THE INVENTION

1. Field of the Invention

The present invention relates generally to fluid delivery devices. More particularly, the invention concerns an improved apparatus having a light activated energy source for infusing medicinal agents into an ambulatory patient at specific rates over extended periods of time.

2. Discussion of the Invention

The oral route is the most frequent route of drug administration. Oral administration is relatively easy for most patients and rarely causes physical discomfort. However, many medicinal agents require a parenteral route of administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow means coupled with electronic based controls and typically involve the use of intravenous administration sets and the familiar bottle or solution bag suspended above the patient. Such methods are cumbersome, imprecise and, generally non-ambulatory requiring bed confinement of the patient. Periodic monitoring of the apparatus by the nurse or doctor is required to detect malfunctions of the infusion apparatus.

Devices of the character from which liquid is expelled from a relatively thick-walled bladder by internal stresses within the distended bladder have also been suggested for infusion of medicaments. For example, such bladder, or "balloon" type devices, are described in U.S. Pat. No. 3,469,578, issued to Bierman and in U.S. Pat. No. 4,318,400, issued to Perry.

A family of highly unique fluid delivery devices has been developed by the present inventor. These novel devices make use of recently developed elastomeric films, expandable foams and similar materials, which, in cooperation with a base define a fluid chamber that contains the fluid to be dispensed. The elastomeric film membrane or the expandable member controllably forces fluid within the chamber into outlet fluid flow channels provided in the device. Elastomeric film membrane devices are described in detail in U.S. Pat. No. 5,205,820 issued to the present inventor. U.S. Pat. No. 5,468,226, also issued to the present inventor, describes various types of expandable cellular elastomers and elastomeric foams used as the energy source of the fluid delivery device for expelling fluid from various physical forms of the fluid delivery device. Because of the pertinence of Pat. Nos. 5,205,820 and 5,468,226, these patents are hereby incorporated herein by reference in their entirety as though fully set forth herein. Copending U.S. application Ser. No. 08/541,030, filed Oct. 11, 1996 in which the present inventor is named as co-inventor, is also pertinent to one form of the apparatus of the invention which is described hereinafter. Accordingly, Ser. No. 08/541,030 is also hereby incorporated by reference as though fully set forth herein.

U.S. Ser. No. 08/919,147, now U.S. Pat. No. 5, 961,492 is also incorporated by reference as though fully set forth herein.

The apparatus of the present invention, which takes various physical forms, makes use of novel light activated expansive material as an energy source. This family of devices can also be used with minimal professional assistance in an alternate health care environment, such as the home. By way of example, devices of the invention can be comfortably and conveniently removably affixed to the patient's body and can be used with or without remotely located infusion sets for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microinfusion rates over time.

One of the embodiments of the present invention comprises an ambulatory fluid dispensing system which includes a relatively thin body attached rigid base assembly and a uniquely designed stored energy means which cooperates with the base assembly for controllably expelling fluid from the reservoir of the device. In this form of the invention, the stored energy means is provided in the form of a light activated gel, the nature of which will be described in greater detail hereinafter. In this particular form of the invention, a novel, remotely located infusion set can be quickly coupled to the base assembly to enable precise infusion of fluid to a patient upon stimulation of the expandable gel by the gel stimulation means of the invention.

Another embodiment of the invention comprises an ambulatory, programmable fluid dispensing system which includes a rigid base assembly and a uniquely designed stored energy means which cooperates with the base assembly for controllably expelling fluid from the reservoir of the device. In this latter form of the invention, the stored energy means is also provided in the form of an expandable gel. A disposable infusion set can be quickly coupled to the base assembly to enable precise infusion of fluid to a patient upon stimulation of the expandable gel caused by operator energization of a battery powered light source.

Another embodiment of the invention comprises an implantable programmable fluid delivery device that also includes an expandable gel which acts as the stored energy means. The expandable gel can be activated by a source of light to cause the gel to controllably expand and expel fluid from the device reservoir through a novel cannula assembly.

The primary thrust of the invention described herein is to provide novel expandable gel type fluid delivery systems that are compact, easy to use, relatively low profile and are eminently capable of meeting even the most stringent of fluid delivery tolerance requirements. In this regard, medical and pharmacological research continues to reveal the importance of the manner in which a medicinal agent is administered. For example, certain classes of pharmacological agents possess a very narrow dosage range of therapeutic effectiveness, in which case too small a dose will have no effect, while too great a dose can result in toxic reaction. In other instances, some forms of medication require an extended delivery time to achieve the utmost effectiveness of a medicinal therapeutic regimen.

SUMMARY OF THE INVENTION

It is an object of the present invention to provide a technically advanced, fluid delivery apparatus for infusing medicinal fluids into a patient that is of a compact, low profile, laminate construction. More particularly, it is an object of the invention to provide an apparatus of such a character which embodies a novel expanding and contracting polymer gel material which uniquely functions as an internal energy source for expelling the medicinal fluids from the device.

Another object of the invention is to provide a fluid delivery device of the character described in the preceding paragraph that can be implanted into the body of the patient.

Another object of the invention is to provide an ambulatory fluid delivery apparatus that can conveniently be used for the precise infusion of various pharmaceutical fluids in accordance with specific therapeutic protocols into an ambulatory patient at controlled rates over extended periods of time.

Another object of the invention is to provide an apparatus of the aforementioned character that is highly reliable and easy-to-use by lay persons in a non-hospital environment.

Another object of the invention is to provide an apparatus that embodies as its stored energy source, a soft, pliable, semi-solid, light activated medium which is activated by a novel light source in a manner to controllably expel fluid from the device over time.

Another object of the invention is to provide an apparatus as described in the preceding paragraph in which the light activated energy source is specifically tailored to provide precise, predictable protocol delivery including pattern delivery of the medicinal agent stored within the reservoir of the device.

Another object of the invention is to provide a fluid delivery system of the class described that includes an interactive sensor means for sensing physiological conditions, such as blood glucose level and patient chemistry.

A further object of the invention is to provide a low profile, fluid delivery device of laminate construction which can meet even the most stringent fluid delivery tolerance and flow signature requirements.

Another object of the invention is to provide stored energy sources of the character described in the preceding paragraph which comprise blends or laminate constructions of phase transition gels that will enable the achievement of multi-rate and multi-frequency delivery protocols.

Another object of the invention is to provide an apparatus of the character described which includes a novel, combination filter and rate control assemblage disposed intermediate the fluid reservoir and the outlet port of the device or intermediate outlet port of the device and the infusion means.

Another object of the invention is to provide an apparatus of the character described which, due to its unique construction, can be manufactured inexpensively in large volume by automated machinery.

Other objects of the invention are set forth in U.S. Pat. Nos. 5,205,820 and 5,468,226, which patents are incorporated herein by reference. Still further objects of the invention will become apparent from the discussion that follows.

BRIEF DESCRIPTION OF THE DRAWINGS

FIG. 14 is an exploded cross-sectional view of a portion of the apparatus shown in FIG. 7 along with a cross-sectional view of the mating delivery line quick disconnect assembly of the invention.

FIG. 14A is an enlarged, cross-sectional view of the components shown in FIG. 14 as they appear in an assembled configuration.

DESCRIPTION OF THE INVENTION

Figure 12:
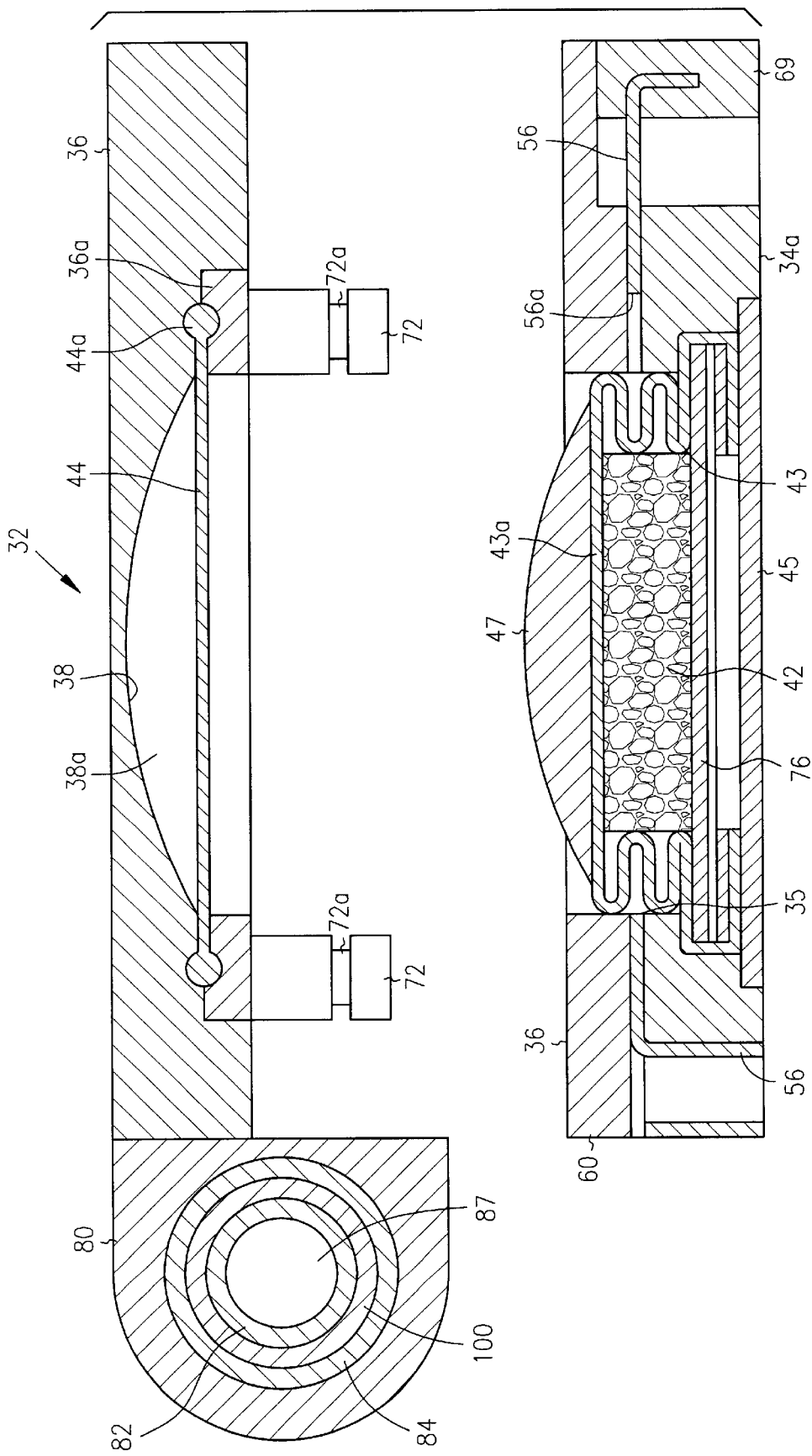
FIG. 12 is an exploded, cross-sectional view of the apparatus shown in FIG. 10.
Figure 13:
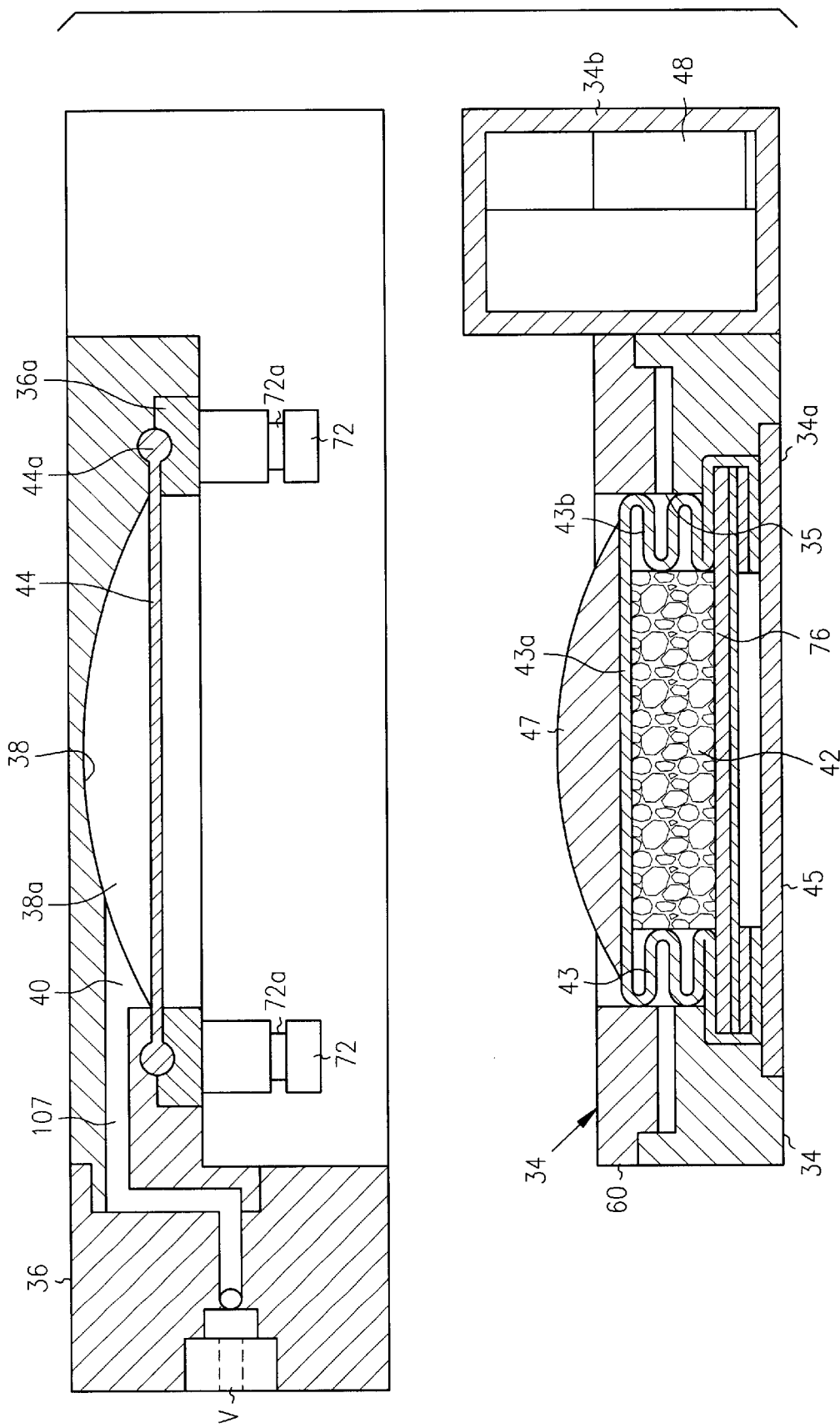
FIG. 13 is an exploded, cross-sectional view of the apparatus shown in FIG. 11.
Figure 15:
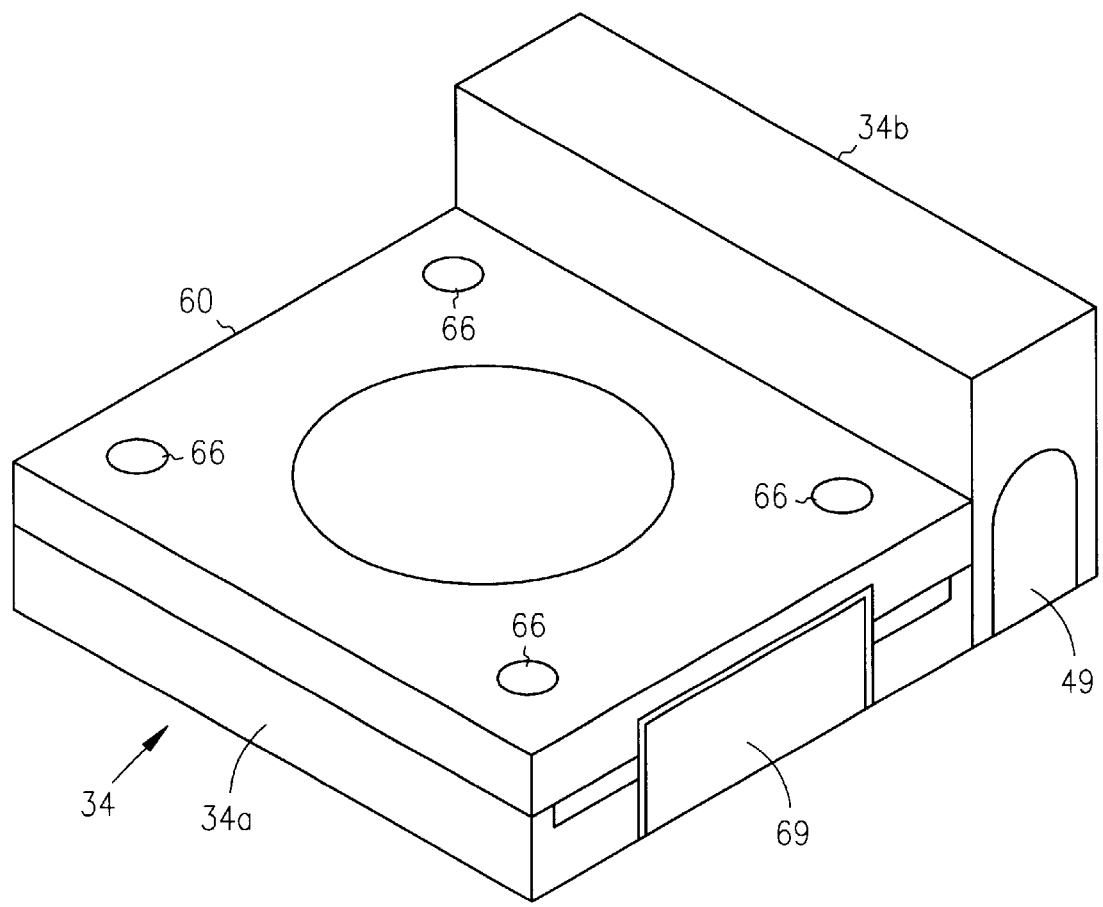
FIG. 15 is a generally perspective, top view of the electronics housing of the apparatus shown in FIG. 1.

Referring to the drawings and particularly to FIGS. 1 through 17, one form of the apparatus of the invention is there shown and generally designated by the numeral 30. This embodiment of the invention comprises two discrete components that can be interconnected together to form the dispensing device of the invention. More particularly, as best seen in FIGS. 12 and 13, the apparatus here comprises a disposable upper reservoir component 32 and a re-usable lower component 34. Reservoir component 32 includes a cover 36 having a cavity 38 which defines the upper boundary of the fluid reservoir of the device (see also FIG. 17).

Figure 11:
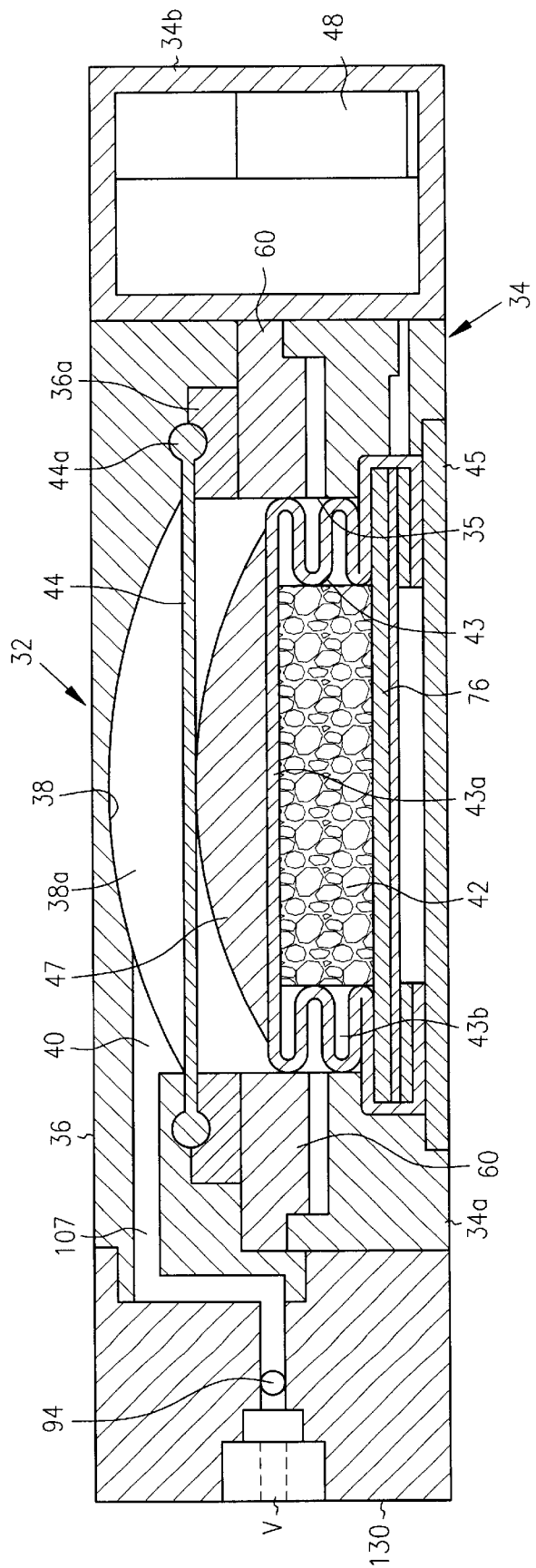
FIG. 11 is a cross-sectional view taken along lines 11—11 of FIG. 1.

Component 34 houses the novel light activated stored energy source of the invention which functions to cause the fluids contained within the sealed reservoir of the device to flow outwardly thereof through an outlet formed in cover 36 (figure 11). The light activated means or stored energy source is here provided in the form of a light activated, expandable polymer mass 42 which is disposed within an expandable metal bellows 43 that is mounted within component 34 in the manner best seen in FIGS. 12 and 13. Expandable mass 42 can take several forms, but a particularly attractive form for devices of the present invention comprises a semisolid form such as a gel.

From a technical viewpoint, gels are often characterized as soft solids which reside in a state between a liquid and a solid state. Frequently gels comprise a cross-linked network of long polymer molecules with liquid molecules trapped within the network. Many gels known in the prior art not only are capable of significantly large volume change in response to stimulus (phase-transition gels), but also exhibit shape memory that substantially enables them to return to their original shape.

Polymer gels can be prepared in a number of ways: by chemical reaction, by the addition of precipitating agents or incompatible solvents, or sometimes, just by the cooling of a sol. Gelatin is a good example of a substance that is readily soluble in hot water and can be gelled by cooling provided that its concentration exceeds 10%. At lower concentrations, the mixture remains a quasi-liquid, the number of cross-links being evidently insufficient to establish a recognizable gel. Gels from synthetic polymers are formed by the polymerization of monomers in the presence of a cross-linking agent from solutions or suspensions to give three-dimensional cross-links between the macromolecules of one component. The second component permeates the network as a continuous phase (the dispersion medium). When the second component is water, the material is called a 'hydrogel'. Because of their biocompatibility, hydrogels are particularly attractive for use in the devices of the present invention.

Figure 23:
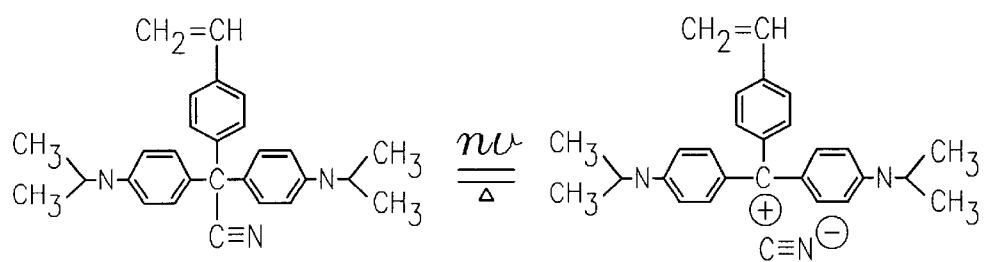
FIG. 23 is a generally diagrammatic view of a typical chemical structure that is sensitive to ultraviolet irradiation.
Figure 24:
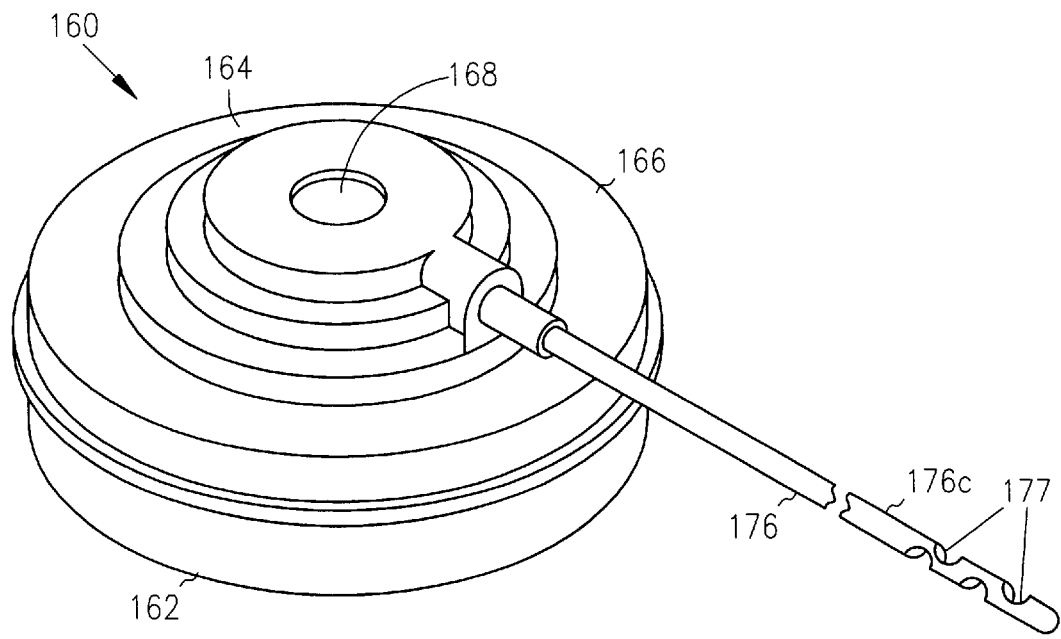
FIG. 24 is a generally perspective view of an alternate form of medicament delivery device that is implantable in the body of the patient.

Phase transition gels best suited for use in constructing the expandable means of the present invention are gels which exhibit a large volume change at a given phase-transition condition. Unlike liquids, which exhibit a fixed temperature for state of vaporization to a known volume and with such vaporization point changing as a function of ambient pressure, the phase-transition gels in this invention are multicomponent polymers which can be made to respond with various volume changes to a singular external stimuli. In this regard, phase transitions accompanied by reversible, discontinuous volume change as large as several hundred times, in response to infinitesimal changes in environmental conditions, have been observed universally in gels made of synthetic and natural polymers. Phase transitions have been induced in gels by varying temperature, solvent composition, pH, ionic composition and a small electric field. Recently, gels sensitive to ultraviolet light were also reported [see, for example, Mamada, A. Tanaka, T., Kungwatchakun, D. & Irie M. Macromolecules 23, 1517–1519 (1990). See also Suzuki, A. and Tanaka, T., Phase Transition In Polymer Gels Induced by Visible Light, NATURE, Vol. 346, 26 Jul. 1990]. The ultraviolet light initiates an ionization reaction in the gel, creating internal osmotic pressure that induces swelling. In the absence of this light, the equilibrium tends towards the neutral polymer system and the gel collapses. This transition process depends on the photochemical ionization and subsequent recombination of ions. Referring to FIG. 23, the chemical structure of Levco derivative molecule bis (4-(dimethylamino) phenyl) (4-vinylphenyl) methyl leucocyanide is there shown. This chemical structure, which is shown, by way of example, is representative of a chemical structure that is sensitive to ultraviolet irradiation.

For certain applications, it is technologically desirable that the transition be induced by faster mechanisms such as visible light. The phase transition of gels induced by visible light, where the transition mechanism is due only to the direct heating of the network polymers by light, provides an extremely fast process.

Examples of suitable phase-transition gels for use in devices of the present invention, are disclosed in Tanaka et al., U.S. Pat. No. Re-35068 and U.S. Pat. No. 5,403,893. Because of the pertinence of these patents, U.S. Pat. No. 5,403,893 and U.S. Pat. No. Re-35068 are hereby incorporated by reference as though fully set forth herein.

While a number of the phase-transition gels described in the Tanaka et al Patents can be used to construct the expandable stored energy means of the present invention, the ionized acrylamide gel compositions therein described are desirable in many applications because of the quite drastic volume change they exhibit in response to an external stimulus such as light. These ionized acrylamide gel compositions comprise a cross-linked, partially ionized polyacrylamide gel wherein between up to 20% of the amide groups are hydrolyzed to carboxyl groups. The gel includes a solvent of a critical concentration at which even a slight change in temperature, pH or salt concentration causes the gel to shrink or swell dramatically. As pointed out by Tanaka et al in the aforementioned patents, the particular critical concentration utilized in the gel composition depends upon the solvent employed, the temperature of the gel and the degree of hydrolysis of the gel. The gel also can contain a positive metal ion such as sodium or magnesium which has the effect of increasing the change in gel volume caused by change of solvent concentration, temperature, pH, or salt concentration.

Another form of phase-transition gel suitable for use in the apparatus of the present invention comprises interpenetrating polymer networks which include a first polymer and a second polymer wherein the second polymer interpenetrates the first polymer. Suitable first and second polymers include polymers which can interact during exposure to a phase-transition condition to thereby cause a significantly large volume change of the gel. Suitable interpenetrating polymer networks can also include more than two polymers. For example, additional polymers can be included in the network which interpenetrate the first and/or second polymers. The nature of these polymers as well as the nature of the interaction between the polymers is discussed in detail in Tanaka, U.S. Pat. No. 5,403,893 and will not here be repeated.

The responsive gels may also be reversibly responsive. For example, when such gels experience certain changes, the entire gel, or a component thereof will undergo a reversible volumetric change which typically involves a shift between two equilibrium states as, for example, expanded and collapsed. This reversible volume change of the entire gel, or a component of the gel may be either continuous or discontinuous. Typically, a continuous volume change is marked by a reversible change in volume that occurs over a substantial change in environmental condition. On the other hand, the gel, or a component thereof, may undergo a discontinuous volume change in which the reversible transition from expanded to collapsed states, and back again, typically occurs over a relatively small change in environmental condition. A gel undergoing a continuous phase-transition may have a similar order to magnitude total volume change as a gel undergoing a discontinuous phase-transition.

Typically, volumetric changes in the phase transition gels result from competition between intermolecular forces, usually electrostatic in nature. Such volumetric changes are believed to be driven primarily by four fundamental forces, that is ionic, hydrophobic, hydrogen bonding and van der Waals bonding interactions, either alone or in combination.

Of particular interest is the fact that gels consisting of copolymers of positively and negatively charged groups may be formulated so that the volume change is governed by more than one fundamental force. In these gels, polymer segments typically interact with each other through ionic interactions and hydrogen bonding.

By way of summary, gels suitable for use as the stored energy sources of the present invention include various cross-linked polymers and gels which can be synthesized from the polymerization of a monomer and a cross-linking agent.

As a general rule, suitable gels can be made from polymers with side groups that can react with a di-or multi-functional cross-linking molecule. However, the simplest system from which gels can be made are polymers with hydroxyl, acid or amine side groups.

By way of non-limiting example, suitable gels for use as the stored energy means may consist, in whole or in part, of polymers made by copolymerizable vinyl monomers. The monomer may include N, N-dissubstituted acrylamides such as N,N-dialkysubstituted acrylamides, or di-N,N substituted acrylamides where the dissubstitution form part of a ring, acrylate ethers, alkyl substituted vinyl ethers, glycol ethers, and mixtures thereof.

Exemplary polymeric gel networks thus may contain poly (N,N-dialkylacrylamide), poly (ethyl acrylate) and mixtures thereof, as well as polymers of N-alkylacrylamide (or analogous N-alkylmethacrylamide) derivatives such as N-ethylacrylamide, N-n-propylacrylamide, N-n-propylmethylacrylamide, or various acrylate copolymers.

Exemplary cross-linking agents may include ethylene glycol diacrylate (EGDA); di(ethylene glycol)bis(allyl carbonate) ("DEGBAC"); methylenebis(acrylamide) ("bis"); ethylene glycol dimethacrylate ("EGDMA"); magnesium methacrylate ("MgMA$_2$") and mixtures thereof. Cross-linkers suitable for polymeric precursors may include diglycidyl ether, divinyl sulfone, epichlorohydrin, phosphoryl chloride, trimetaphosphate, trimethylomelamine, polyacrolein, and ceric ion redox systems, although the most preferred of these will not have active hydrogens. The cross-linking agent effects partial cross-linking of the polymer and provides a means to control the gel's mechanical strength, swelling degree, and intensity of volume change trigger by changing the cross-linking density. Cross-linking of linear polymers by chemical reagents is preferred for gels made from biological polymers such as cellulose ethers. Preferred cross-linkers for polysaccharide gels, especially cellulose ethers, are multifunctional carboxylic acids, such as adipic acid (hexanedioic acid: $HOOC(CH_2)_4COOH$), succinic acid ($HOOC(CH_2)_2COOH$), malonic acid (propanedioic acid: $CH_2(COOH)_2$, sebacic acid (decanedioic acid: $HOOC(CH_2)COOH$), glutaric acid (pentanedioic acid: $HOOC(CH_2)_3COOH$), or, 10 decanedicarboxylic acid.

Also of interest as possible gel materials for use with the apparatus of the present invention are the "four-armed" polyethylene glycol (PEG) gels discussed in an article entitled "Light-Induced Tailoring of PEG-Hydrogel Properties" by Fotios M. Andreopoulos, et al in *Biomaterials* 19 (1998) 1343–1352. As discussed in this article, when the hydroxyl termini of PEG gels are functionalized with cinnamylidene acetate groups, photosensitive PEG macromers (PEG-CA) are formed. Upon radiation of the macromers, crosslinks are formed between adjacent cinnamylindene groups resulting in highly crosslinked networks which exhibit photoscissive behavior upon exposure of UV irradiation (254 nm). These PEG gels as well as the others discussed herein are cited by way of example and not by way of limitation.

While the PEG gels in themselves do not exhibit reversible swelling upon exposure to UV light, they can be modified to do so by copolymerization with UV sensitive monomers of the type shown in FIG. 23 and previously described herein.

Other polymer gel systems that could swell reversibly, would incorporate UV active monomers of the character previously described as phase transition gels. For example, Tanaka et al has copolymerized the Levco derivative into acrylamide gels in the manner earlier discussed herein.

Another suitable photoactive monomer based on the azobenzene derivative $CH_2CHC(O)C_6H_4N=NC_6H_5$ has also been incorporated into UV active phase transition gels as demonstrated by M. Irie in *New Functional Materials*, Volume B in an article entitled "Photo-and Chemical-Responsive Polymer Solution and Gel Systems".

Suitable monomers for copolymerization with the UV active monomers previously mentioned are: first common methacrylates such as hydroxymethacrylate (HEMA) n-isopropylacrylamide (NIPPAAm), N, N'- methylenebis (acrylamide) (BIS) and other commercially available acrylate and methacylate monomers. Polyethylene glycol-methacrylate (PEGMA) could also be copolymerized with the UV active monomers mentioned in the preceding paragraphs.

Polyethylene oxides (PEGs) can also be used in modified form to act as crosslinkers in polymerizations to form photoactive gels. For example, commercially available PEGs of the character previously described herein can be modified to yield PEG-diamines for copolymerizaton with acrylates following the protocol described by Mooney, (Macromolecules, 1999, Volume 32, P. 5561). Other methacrylate derivatized polymer gels that should allow facile incorporation of the photoactive monomers include glycidyl methacrylate-derivitized dextran (see Hennink, W. E., Macromolecules, 1997, 30,4639.); lactose-based homopolymers in the presence of an acrylate crosslinker (see Zhou, W. J., Macromolecules, 1999, 30, 7063) and polyethylene glycol diacrylates (PEGDA) (see Cha Hesj, P. R. Macromolecules, 1996, 29, 1976). The photoactive monomers could also be polymerized with a vinyl lactam such as N-vinylcaprolactam in the presence of a standard crosslinker such as a vinyl pyrolidone.

Returning now to a consideration of the initial form of the apparatus of the invention and referring particularly to FIGS. 12 and 13, sealing means 44 spans and sealably closes cavity 38 to form the fluid reservoir 38a of the device. This sealing means here comprises a distendable membrane 44 having an O-ring like periphery 44a that is urged into sealable engagement with the peripheral portion of cover 36 by a membrane retaining ring 36a that is connected to cover 36. When membrane 44 is in place, reservoir 38a can be filled with the fluid to be dispensed by novel fill means the character of which will presently be described. When mass 42 is activated by a suitable light source, it will controllably expand from the compressed configuration shown in FIGS. 10 and 11 to the expanded configuration shown in FIG. 11A and, in so doing, will experience a change in volume.

Figure 10:
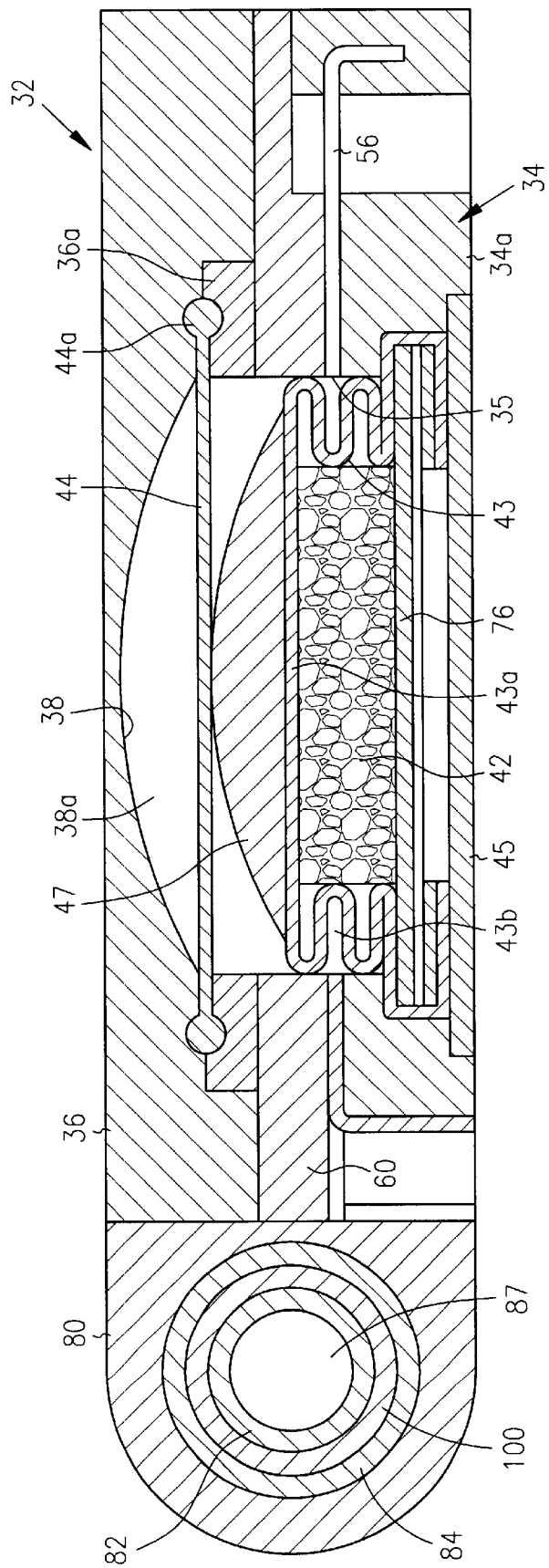
FIG. 10 is a cross-sectional view taken along lines 10—10 of FIG. 1.
Figure 11A:
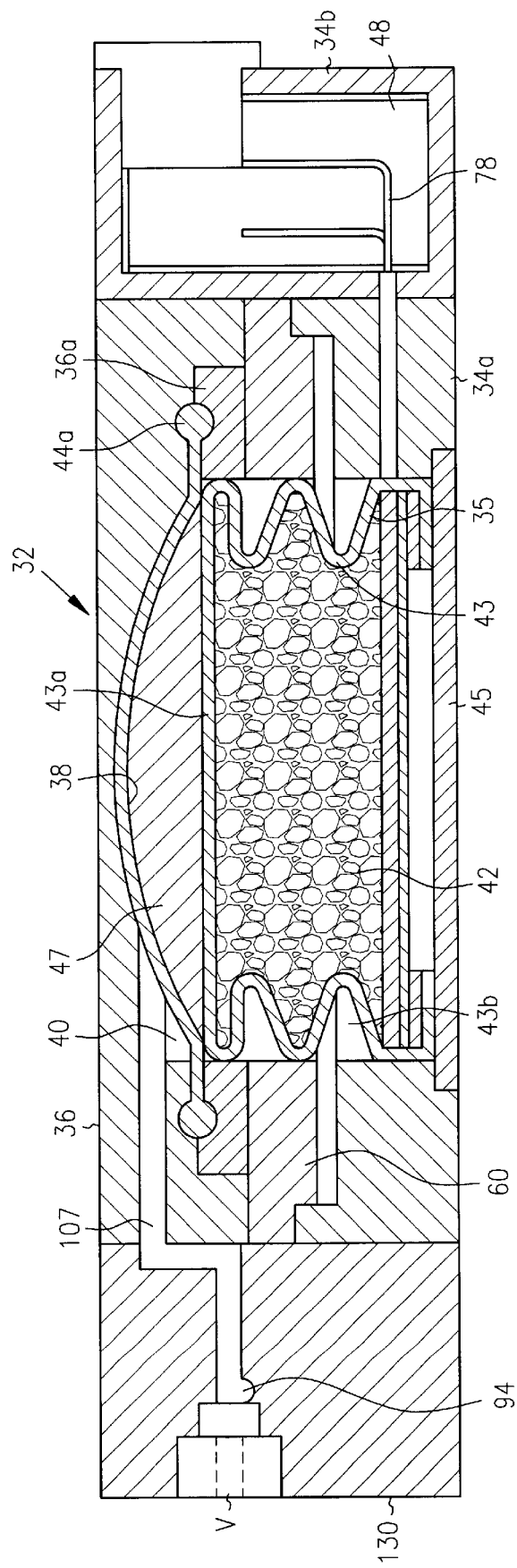
FIG. 11A is a cross-sectional view similar to FIG. 11, but showing the gel in an expanded condition.

With the construction described in the preceding paragraphs and as illustrated in FIGS. 10 and 11, when the reservoir is filled, mass 42 will be compressed by a generally dome-shaped pusher member 47 which engages the upper surface 43a of bellows 43. Then, following activation of expandable means 42, the expandable mass will controllably expand within bellows 43 urging pusher member 47 into engagement with sealing membrane 44. Membrane 44 will, in turn, act on the medicinal fluid that is contained within the reservoir in a manner to controllably force it outwardly thereof through outlet passageway 107 and into the infusion means of the apparatus, the details of construction which will be described hereinafter.

Figures 16, 16A:
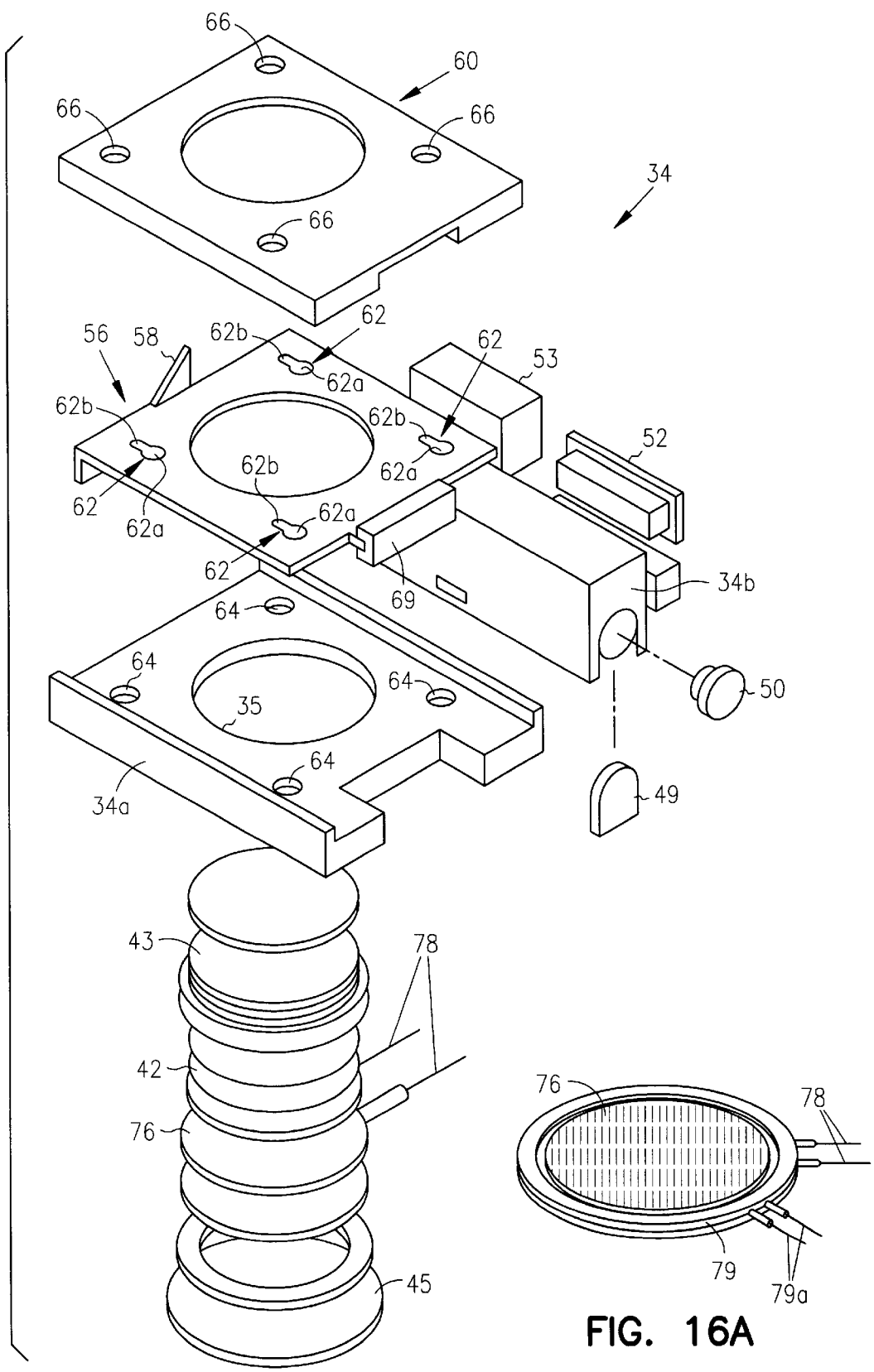
FIG. 16 is a generally perspective, exploded view of the electronics housing shown in FIG. 15.
FIG. 16A is an enlarged, generally perspective view of the light source and heater component of the invention.

As best seen in FIGS. 12, 13, and 16, the re-usable component 34 includes a base member 34a and an electronics housing 34b, which is connected thereto. Base member 34a includes an opening 35 that is adapted to closely receive the lower portion of bellows 43. Opening 35 is closed by a cover plate 45 that cooperates with base member 34a to form a hollow, bellows containing chamber 43b.

Electronics housing 34b includes a chamber 48 which houses the power supply and which can be closed by a cover 49 (see FIG. 16). The power supply can take various forms, but is here provided as a high performance mercury or lithium battery 50 that is of conventional construction and is readily commercially available from sources such as Battery Engineering, Inc. of Cranton, Mass. Electronic housing 34b also houses the electronic control module 52 of the device and the light drive module 53, the character of each will presently be described. As will later be discussed, module 52 can be programmed by means of the electronic programming button impulse switches 54 carried by housing 34b (FIG. 2).

Figure 2:
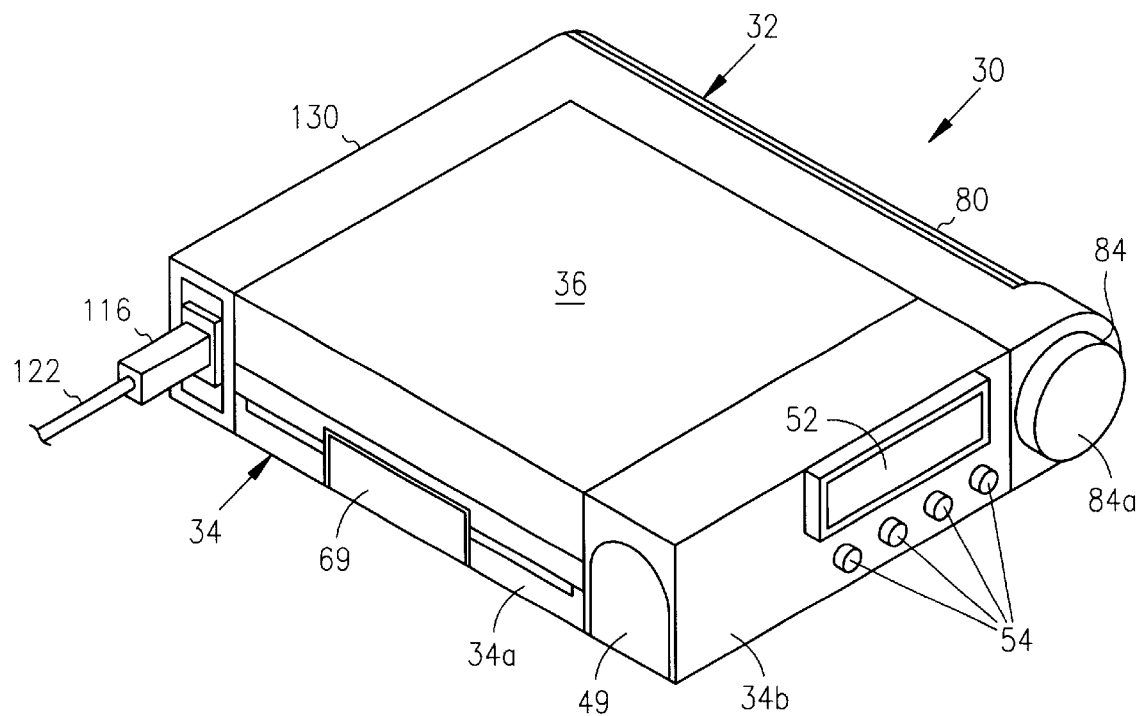
FIG. 2 is a generally perspective front view of the device shown in FIG. 1.
Figure 3:
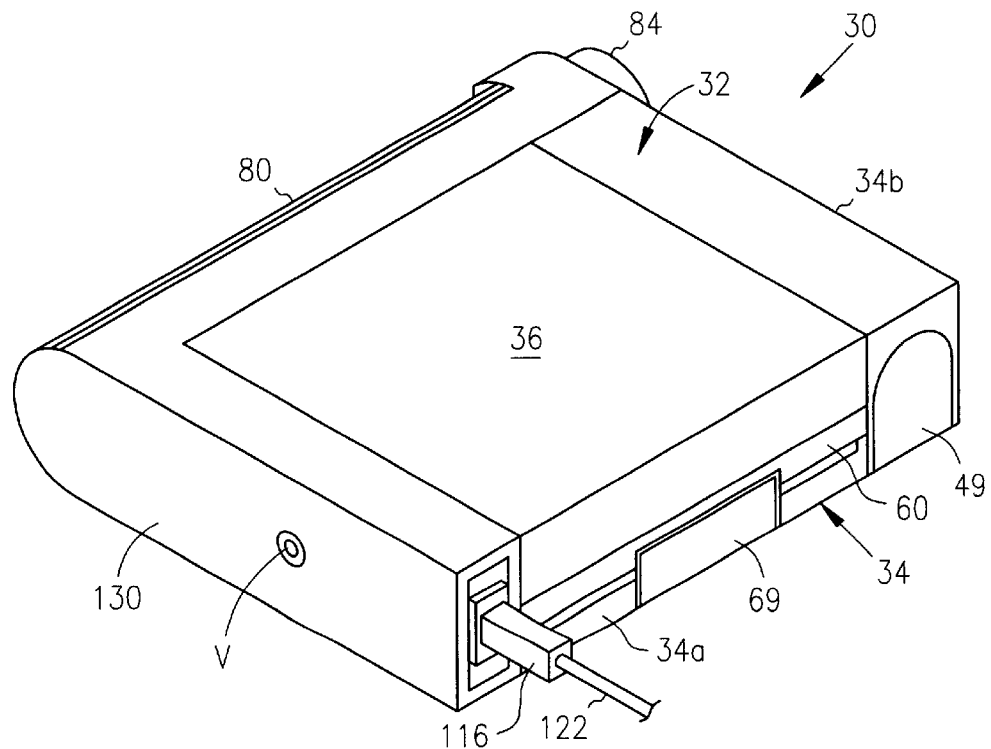
FIG. 3 is a generally perspective right-side view of the device shown in FIG. 1.

Superimposed over base member 34a is a locking plate 56 (FIG. 16), which comprises part of the component connector means of the invention, and which functions to releasably interconnect reservoir component 32 with electronics component 34 in the manner shown in FIGS. 2 and 3. Locking plate 56, which includes an operating spring tab 58, the purpose of which will presently be described, is held in position by a retainer plate 60 which overlays base member 34a in the manner shown in FIGS. 12 and 13. As shown in FIG. 16, locking plate 56 includes a generally oval shaped central clearance opening 56a and four generally keyhole-shaped openings 62, each of which has an enlarged diameter portion 62a. Portions 62a can be moved into index with one of four bores 64 formed in base member 34a and with one of four apertures 66 formed in retainer plate 60 by pushing locking plate 56 inwardly against the urging of spring 58.

Figure 20:
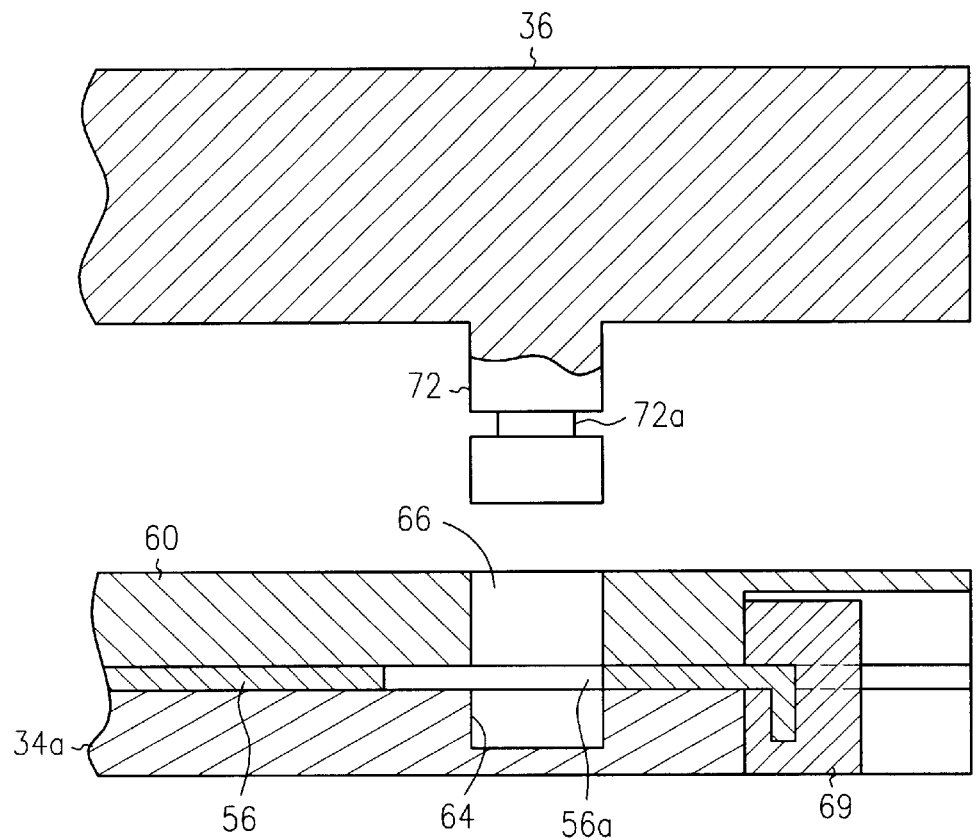
FIG. 20 is a fragmentary, cross-sectional view showing the construction of the locking mechanism for connecting together the components shown in FIG. 18.

More particularly, as illustrated in FIG. 20, by pushing inwardly on a push pad 69 provided at the edge of plate 56, spring tab 58 will be compressed and the enlarged diameter portions 62a of keyhole-shaped openings 62 will move into index with bores 64 and with apertures 66. However, when pressure on push pad 69 is released, resilient spring 58, will return to its starting position and concomitantly will urge locking plate 56 toward its starting position, causing the neck portions 62b of openings 62 to move into index with bores 64 and apertures 66.

Figure 21:
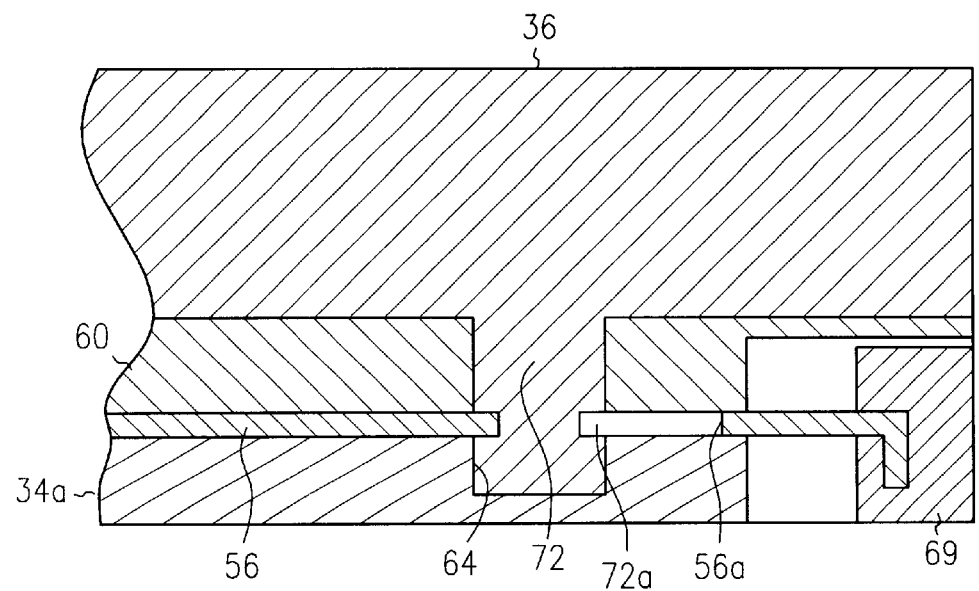
FIG. 21 is a fragmentary, cross-sectional view showing the components illustrated in FIG. 20 in an assembled configuration.

With the construction thus described, when push pad 69 has been pushed inwardly connector pins 72 provided on the reservoir component can be freely inserted into apertures 66, past locking plate 56 and into bores 64 of base member 34a. Once the pins are fully seated within bores 64, a release of pressure on push pad 69 will cause spring 58 to urge locking plate 56 into the position shown in FIG. 21. In this position, the edges of the necked down portions 62b of the keyhole-shaped openings 62 will reside within grooves 72a formed in connector pins 72 thereby locking together reservoir component 32 and electronics component 34. When desired, the components can be separated by pushing inwardly on push pad 69 to move enlarged diameter portions 62a into index with bores 64 and apertures 66.

When the reservoir and electronic component 32 and 34 have been connected in the manner shown in FIGS. 2, 3, 10, and 11, light actuated gel 42 can be activated in a manner next to be described. When activated, the gel will controllably expand urging the fluid to be dispensed to the patient outwardly of the device reservoir which is formed upon filling the dispensing device using the reservoir fill means of the invention.

Considering now the novel activating means of the invention for activating gel 42, this important means here comprises a light sheet that is carried within chamber 43b and is generally designated by the numeral 76. Light sheet 76 is commercially available from sources including Lightsheet Systems of Nashua, New Hampshire and comprises flexible electroluminescent film having, a micro-thin layer of light-generating phosphor compound laminated within electrically-conductive and insulating materials. Power is supplied to the lightsheet through two terminals 78 nominally spaced 0.20 inches apart mounted at one end thereof. When energized light is distributed across the entire sheet, charging the internal phosphor layer to a light-emitting state causing the light sheet to emit a bright white light over substantially its entire surface. The manner of energizing the light sheet will be described hereinafter. The color and intensity of the light source can be appropriately tailored to the required local level of environmental requirement.

Surrounding light sheet 76 is a heater means for maintaining the expandable gel 42 at substantially a constant temperature. This heater means is here provided as a foil heater 79 that circumscribes light sheet 76 in the manner shown in FIGS. 16 and 16A. Power is supplied to the heater foil through two terminals 79a that are spaced apart and appropriately connected to the heater foil in the manner in FIGS. 16 and 16A. When energized the heater foil will heat the expandable gel to a pre-determined, substantially constant temperature to enable appropriate expansion thereof upon stimulation by the light source. The temperature to which the gel is heated is, of course, dependent upon the type of gel being used. It should be understood that some gel forms do not require heating.

Figure 12A:
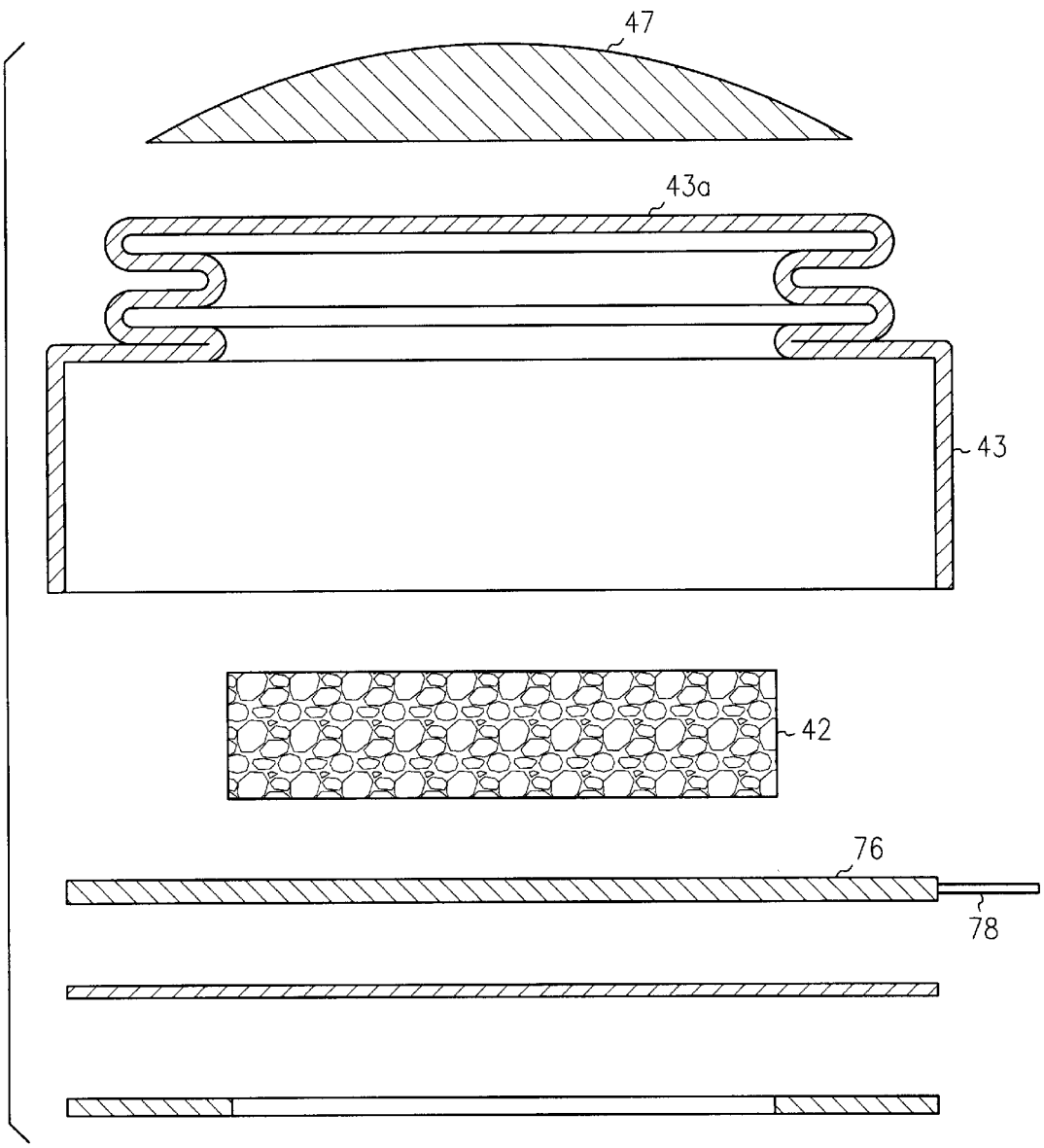
FIG. 12A is an exploded, cross-sectional view of the gel, bellows and pusher assembly of the invention.
Figure 12B:
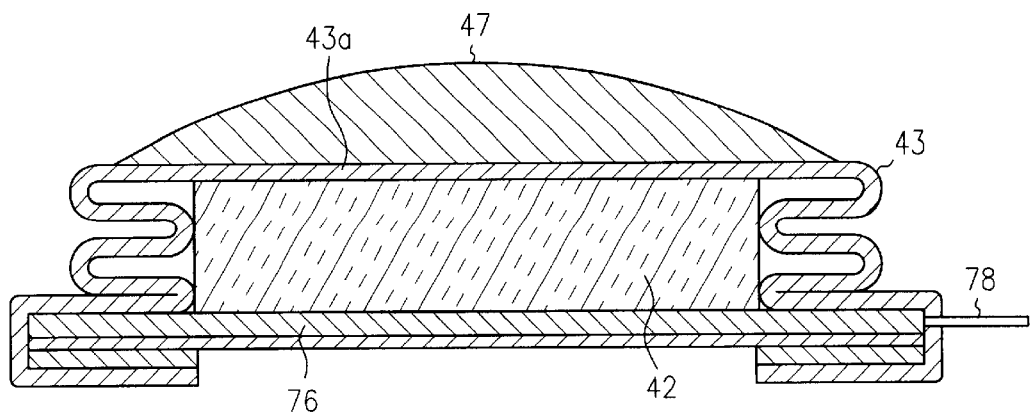
FIG. 12B is a cross-sectional view of the gel, bellows and pusher assembly in a relaxed assembled configuration.

Light sheet 76 rests upon a protective disk 76b of suitable material which, in turn, is supported by a silicone gasket 76c (FIGS. 12A and 16). Base plate 45 which engages gasket 76c functions to sealably close chamber 43b.

Figure 6:
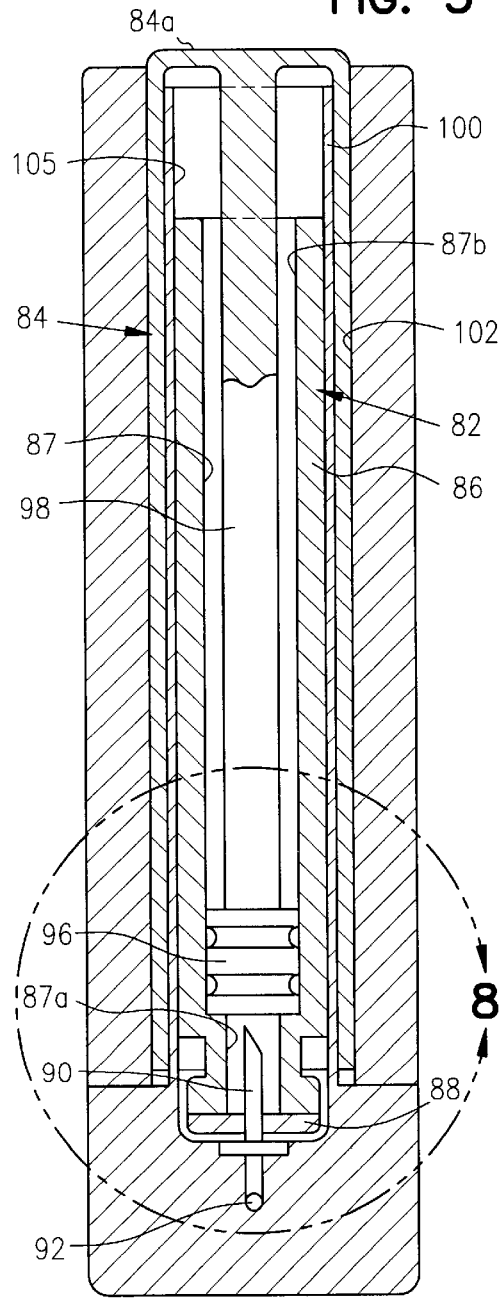
FIG. 6 is cross-sectional view taken along lines 6—6 of FIG. 1.
Figure 7:
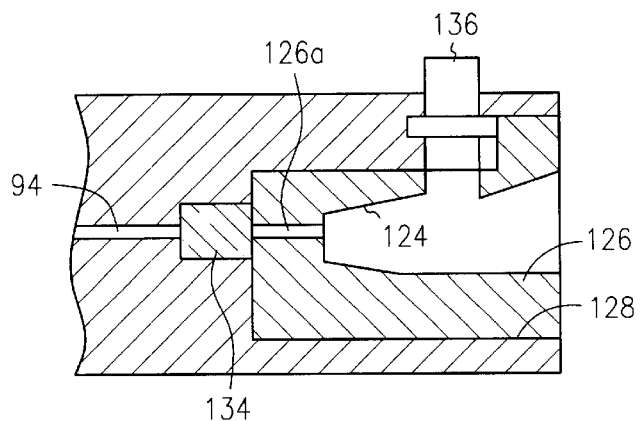
FIG. 7 is a cross-sectional view taken along lines 7—7 of FIG. 1.
Figure 8:
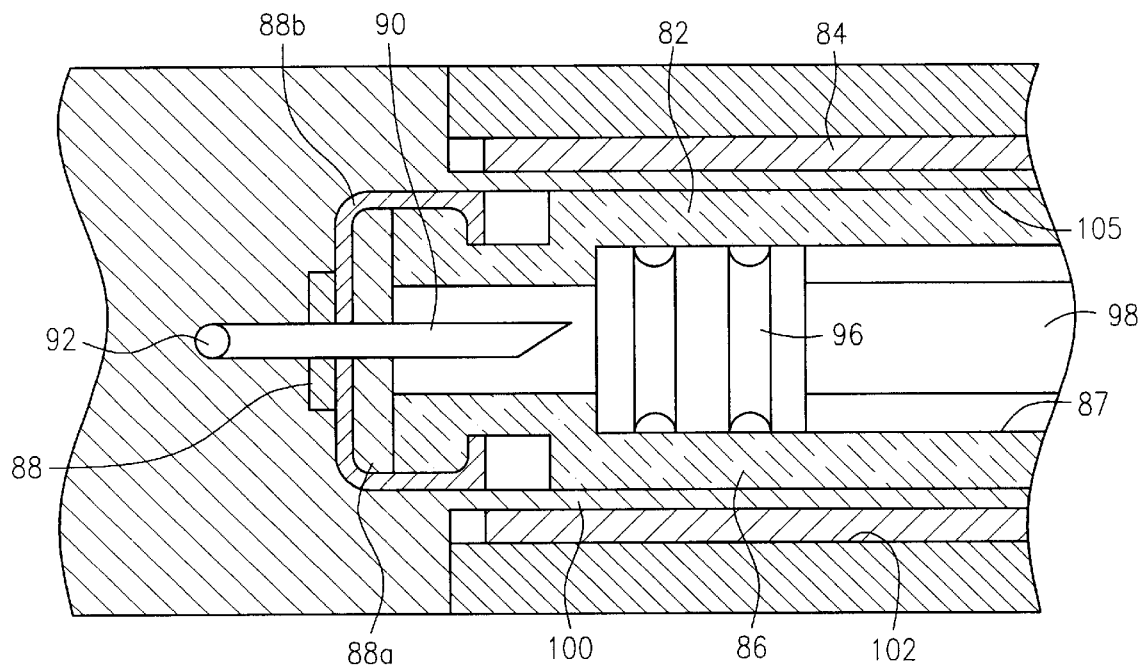
FIG. 8 is a cross-sectional view of the area designated as 8 in FIG. 6.
Figure 9:
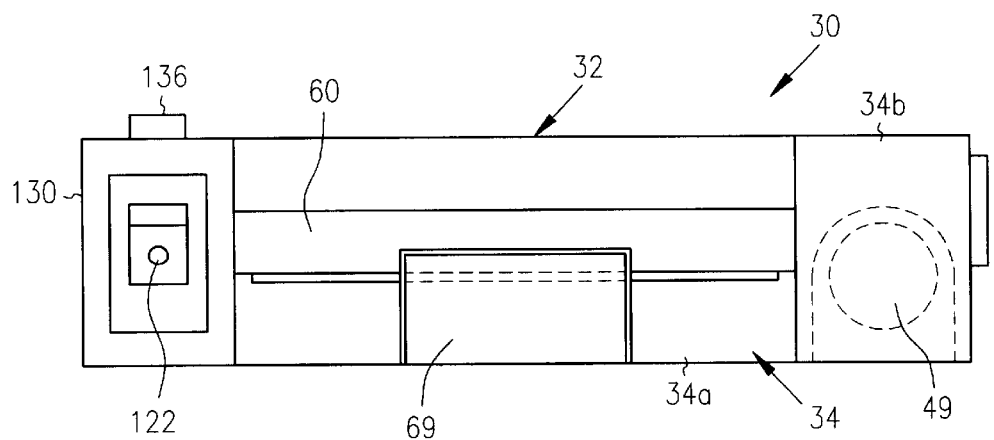
FIG. 9 is a right side view of the device shown in FIG. 1.

Considering next the novel reservoir fill means of the invention, this means here comprises three major components, namely a side housing 80 connected to cover 36, a medicament vial cartridge or container assembly 82 and an adapter or pusher sleeve assembly 84 (FIGS. 6 and 8). Container assembly 82 contains the medicinal fluid with which the reservoir of the dispensing device is to be filled. As best seen in FIG. 6, container assembly 82 includes a container or vial cartridge 86 having a chamber 87. Chamber 87 has first and second open ends 87a and 87b. The first open end 87a is sealably closed by closure means, here provided in the form of septum assembly 88 which includes a pierceable septum 88a and a clamping ring 88b for connecting the septum to the container proximate the first open end (FIG. 8). Septum 88a is pierceable by a cannula means or cannula 90 that is carried by side housing 130.

To expel fluid from chamber 87 of the container assembly into cannula 90 and thence into the fluid reservoir of the dispenser unit via passageways 92, 94 and 107 (FIG. 1), displacement means are provided. This displacement means here comprises a plunger 96 that is telescopically movable within chamber 87 by pusher sleeve assembly 84. To accomplish this movement, pusher sleeve assembly 84 is provided with pusher means shown here as a pusher rod 98 which is integrally formed with end wall 84a of the pusher sleeve assembly (FIG. 6).

Referring particularly to FIGS. 6 and 8, it is to be noted that side housing 80 includes an inner, generally cylindrically shaped wall 100 which defines an elongated annular space 102 within which the pusher sleeve assembly 84 is slidably received. As shown in FIGS. 6 and 8, container assembly 82 is closely receivable within a chamber 105 formed internally of wall 100 and can be urged forwardly of chamber 105 by inward telescopic movement of the pusher sleeve assembly into annular space 102. More particularly, as indicated in FIG. 8, the inboard end of pusher rod 98 engages plunger 96 and urges it inwardly of chamber 87 as the pusher sleeve is moved inwardly of annular space 102.

Figure 1:
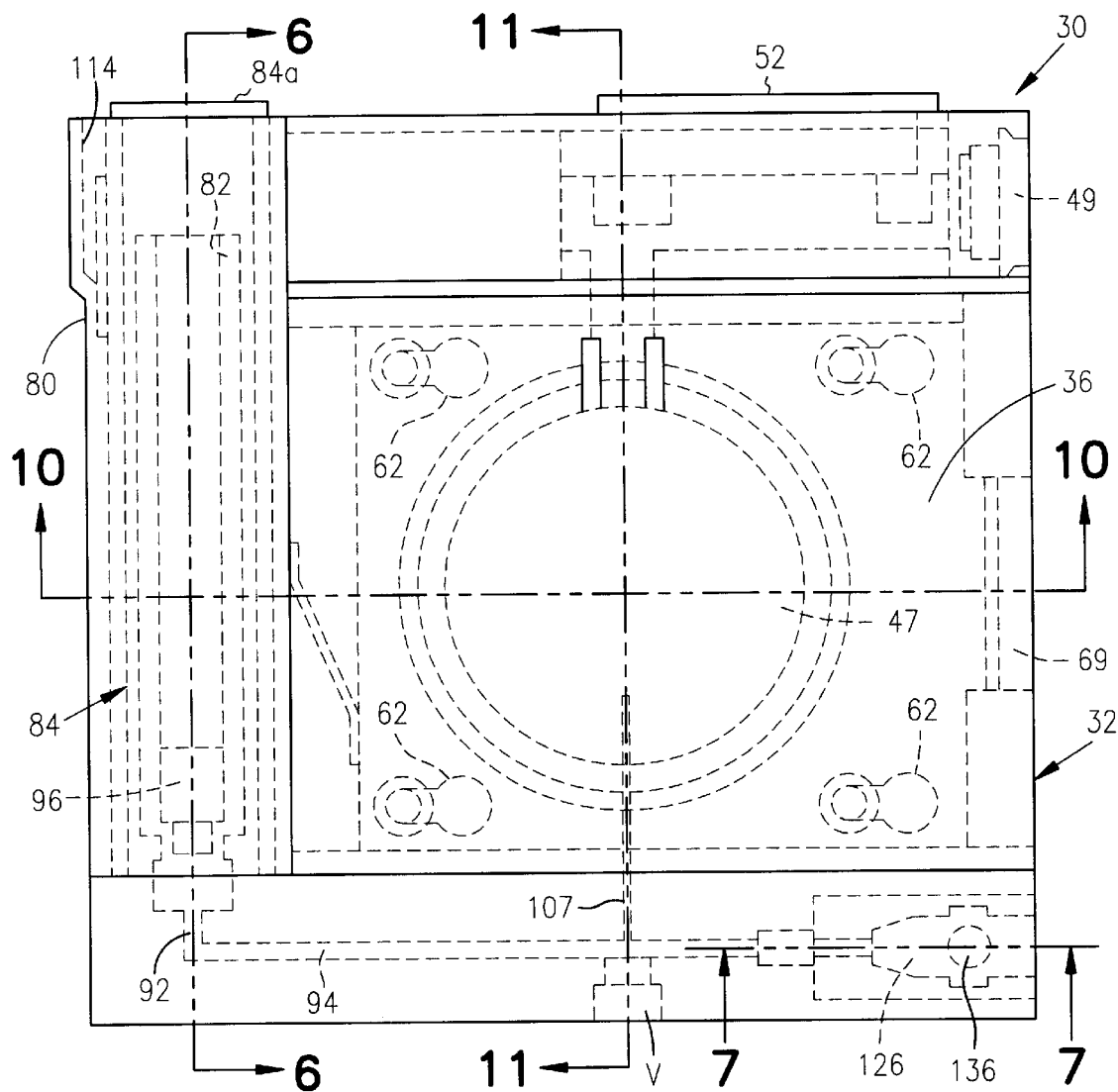
FIG. 1 is a top plan view of one form of the fluid delivery apparatus of the invention.

During the initial mating of the pusher sleeve assembly and the container assembly with side housing 80, the resistance of the fluid within chamber 87 will resist movement of plunger 96 inwardly of chamber 87 so as to cause the entire container assembly to initially move inwardly of chamber 105 to a position wherein the septum assembly 88 is engaged by cannula 90 of the side housing. A continued inward force on the pusher sleeve assembly will cause cannula 90 to pierce the septum in the manner shown in FIG. 8, thereby opening fluid communication between chamber 87 of the container assembly and the internal fluid passageway of cannula 90. Once the septum has been pierced, pusher rod 98 will urge plunger 96 forwardly of chamber 87 from a first location proximate the second open end to the second location shown in FIG. 8. As plunger 96 moves forwardly of chamber 87, fluid within the chamber will be caused to flow into the central fluid passageway of cannula 90 toward a passageway 92 formed in side house 130 and finally into the device reservoir via passageways 94 and 107 (FIG. 1).

Figures 17, 17A:
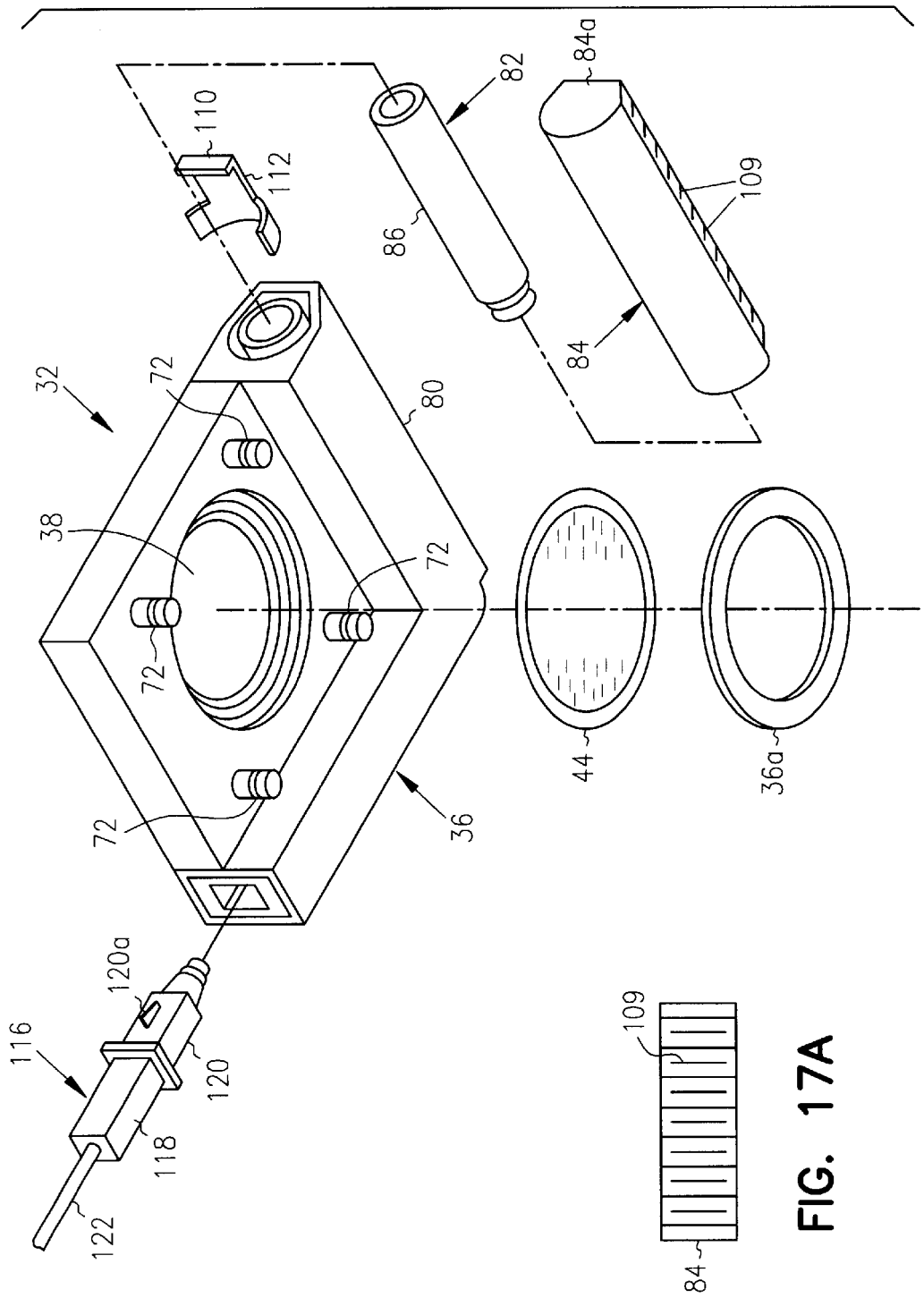
FIG. 17 is a generally perspective, bottom view of the fluid reservoir housing of the apparatus shown in FIG. 1.
FIG. 17A is a bottom view of the pusher sleeve assembly showing the locking teeth formed thereon.
Figure 18:
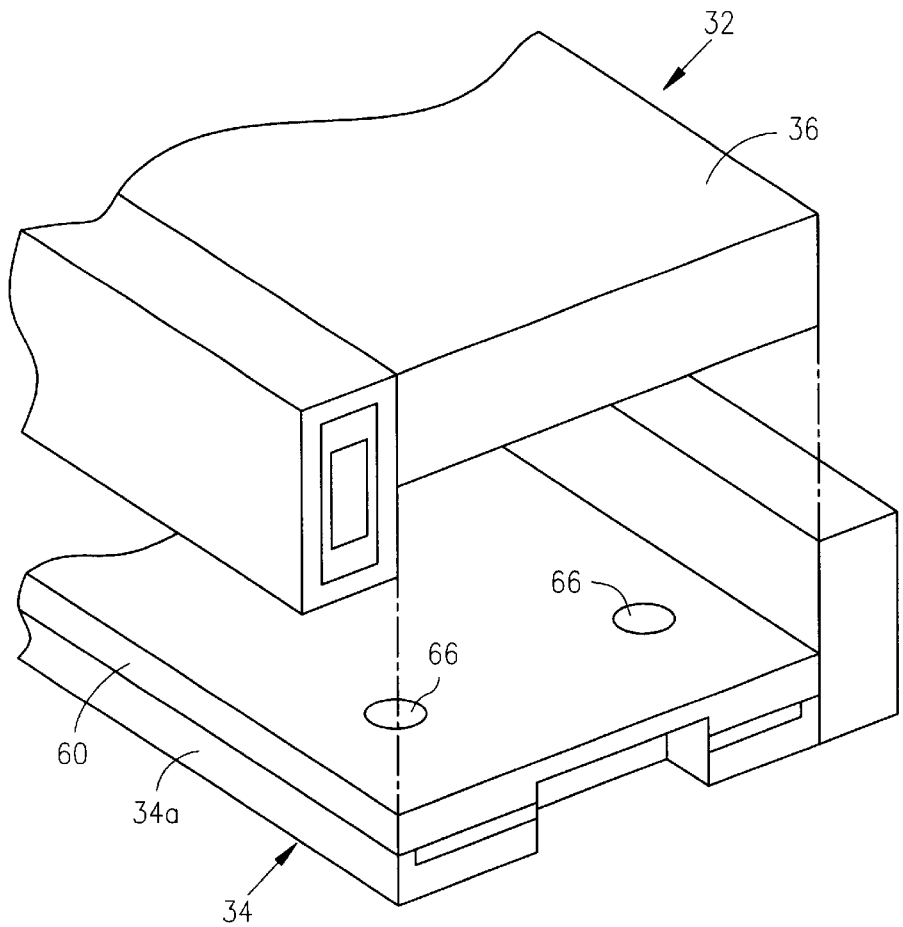
FIG. 18 is a generally perspective, fragmentary exploded view of the electronics housing and fluid reservoir housing portions of the apparat 1.
Figure 19:
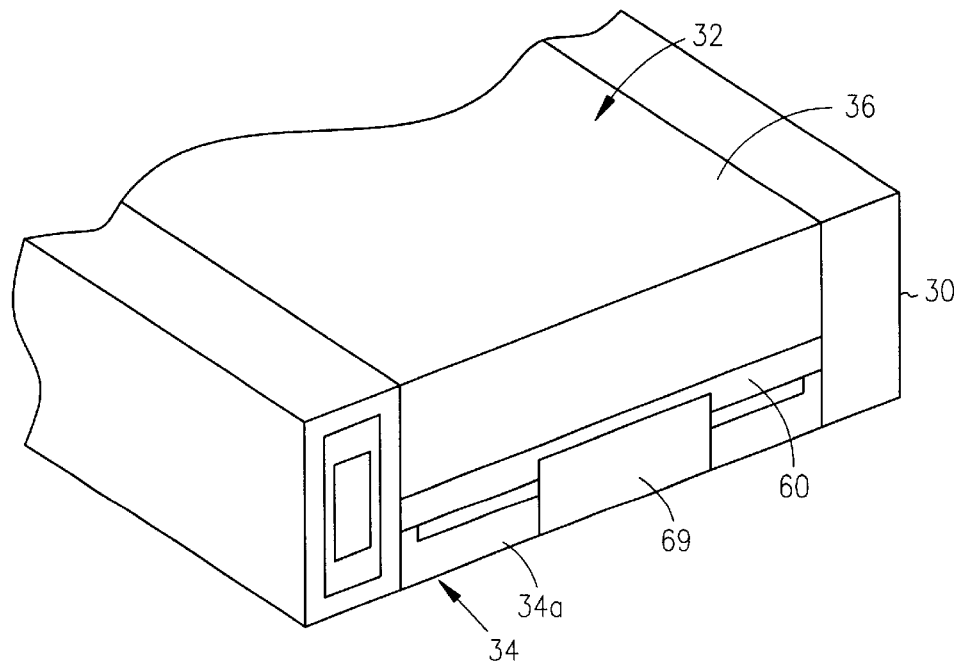
FIG. 19 is a generally perspective, fragmentary view of the components shown in FIG. 18 as they appear in an assembled configuration.

As indicated in FIGS. 17 and 17A, pusher sleeve assembly 84 includes a plurality of longitudinally spaced locking teeth 109 which are engaged by a locking tab 110 provided on a clip-like member 112 that is mounted within a space 114. As the pusher sleeve assembly is urged into annular space 102, tab 110 will ride over teeth 109. However, teeth 109 are configured to prevent attempted removal of the pusher sleeve thereby preventing re-use of the fill means.

Figure 4:
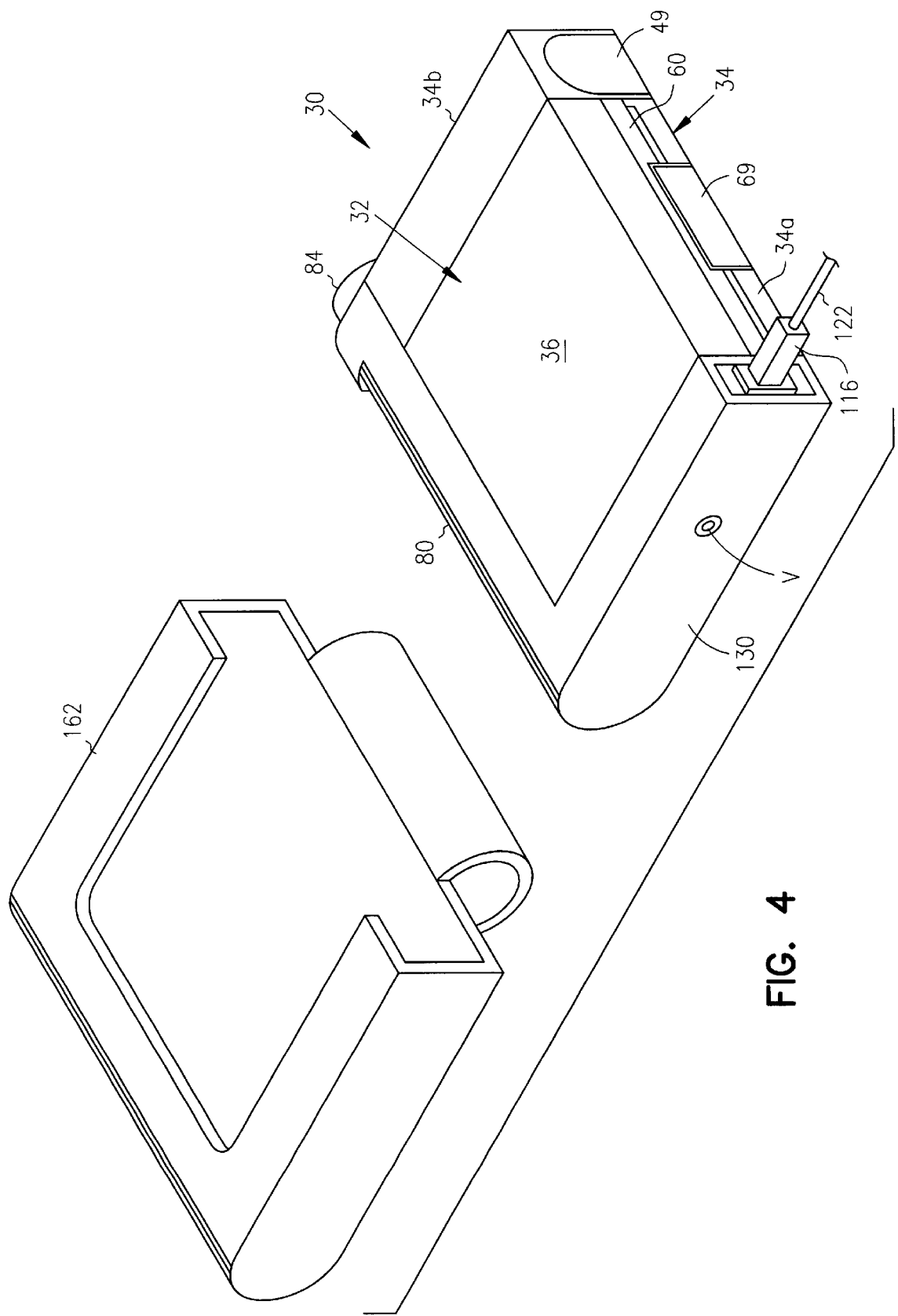
FIG. 4 is a generally perspective right side view of the device shown in FIG. 1 along with a generally perspective view of a belt clip for receiving the device to enable it to be affixed to the user's belt.
Figure 5:
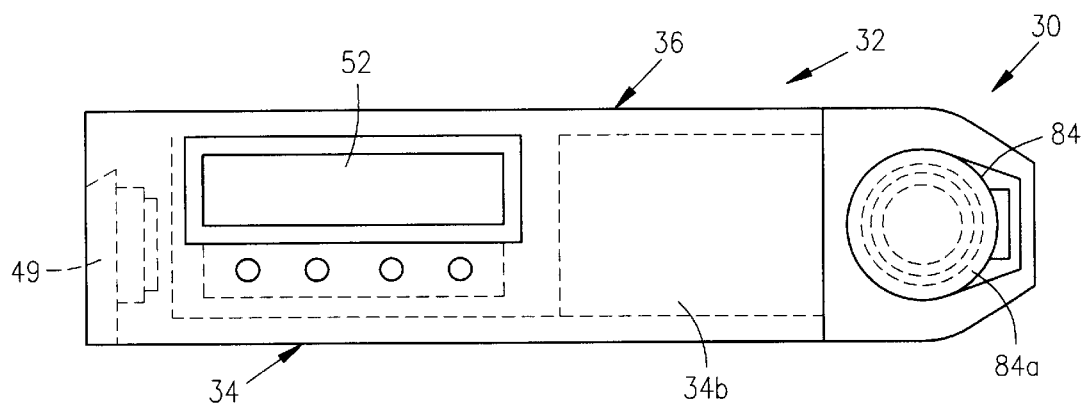
FIG. 5 is rear view of the device shown in FIG. 1.

Following filling of the reservoir of the device with the fluid to be infused into the patient, the novel infusion means of the invention is releasably connected to reservoir component 32 by quick connect means in the manner shown in FIGS. 3 and 4. As indicated in FIG. 14, the quick connect means here comprises line connector 116 that includes a body 118 having a fluid passageway 120 there-through. Connected to the outboard end of passageway 120 is a conventional administration set delivery line 122. The forward portion of body 118 is sealably received within a tapered bore 124 formed in a connector block 126. Connector block 126 is, in turn, received within a cavity 128 formed in a second side housing 130 that is connected to cover 36. Cavity 128 is in communication with the reservoir of the device via passageways 94 and 107 (FIG. 1). When connector block 126 is in position within cavity 128, passageway 126a formed in connector block 126 is in communication with passageway 94 via the flow control means of the device. This flow control means here comprises a porous impedance frit 134 which functions to controllably impede or modulate fluid flow toward line 122 in the event of any unexpected environmental perterbation and during the reservoir filling step. Body 118 of line connector 116 further includes a resilient tab 120a (FIGS. 14 and 14A) which is engaged by a release button 136 that releasably secures the line connector in position within the connector block.

In operation of the apparatus of this latest embodiment of the invention, after the reservoir has been filled and the infusion means connected in the manner just described, the electronic controller and storage module of the device can be programmed to enable the precise delivery of basal, elevated basal, bolus and varying dosing volumes over time in response to either a physiological sensor of the character previously described or to a programmed delivery protocol, such as a preprogrammed protocol can also include specific pattern delivery with alternate pulse widths, frequency, duration, and timing against known and clinically established values. The electronic controller can also be programmed to indicate function status to the user.

Figure 22:
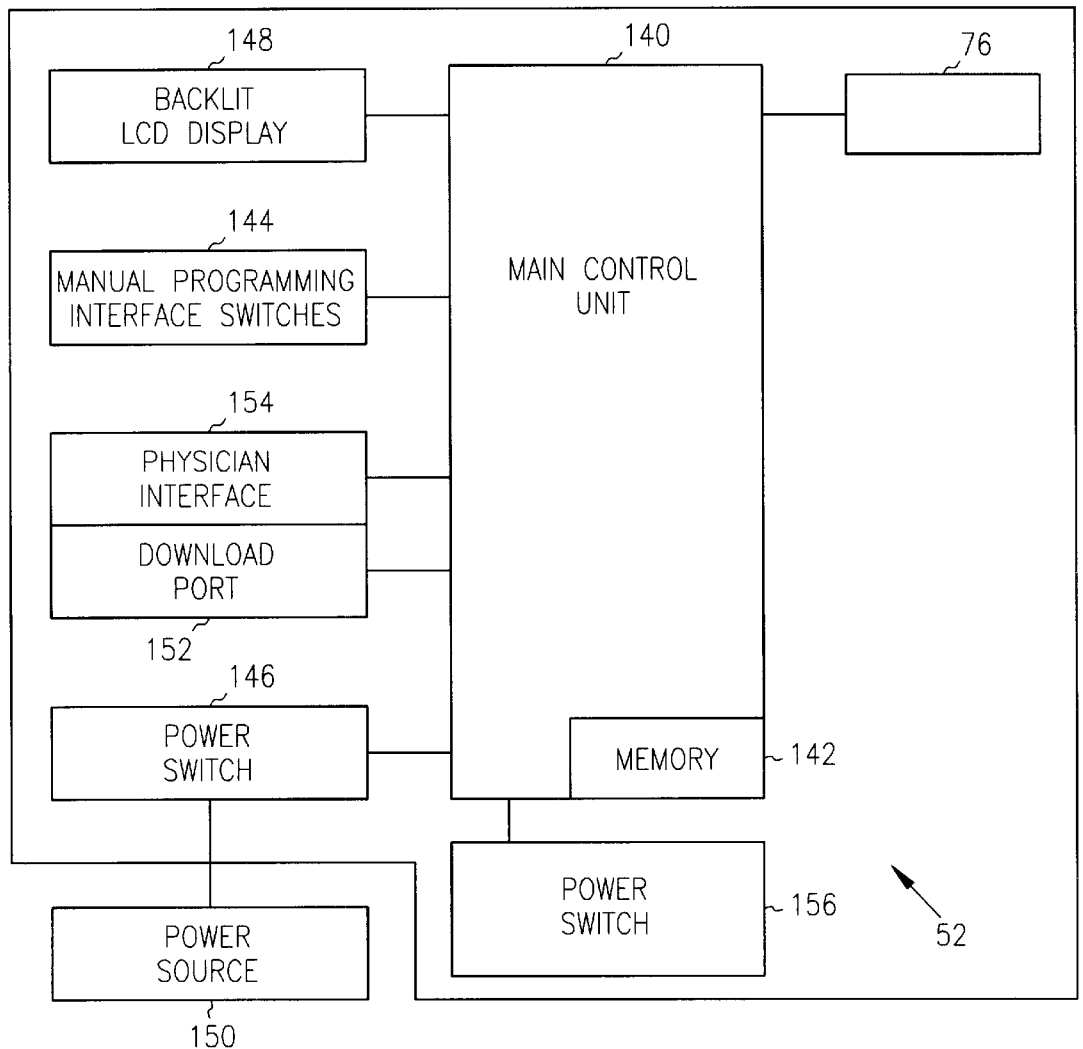
FIG. 22 is a generally diagrammatic view showing the relationship among the various components of the controller and stimulation means of this initial latest embodiment of the invention.

Referring particularly to FIG. 22, it can be seen that the electronic controller module 52 comprises a main control unit 140 having a memory 142, manual programming interface switches 144, the conventional power source or battery 50 and a power switch 146. Also connected to main control unit 140 is a data display shown here as a backlit LCD display 148, a download port 152, a physician's interface 154 and a real time clock 156. Additionally, the light sheet 76, the foil heater 79 and an interactive sensor 157 are also connected to the main control unit in the manner shown in FIG. 22. After the electronic controller and storage means are initially programmed, programming buttons 54 (FIG. 2), which are operably associated with switches 144, can be used to select a different delivery schedule. If desired, once the unit is programmed, the controller can be locked using the physician's interface thereby preventing any changes to the settings by an unauthorized person. It is to be understood that electronic controller module 52 can readily be programmed by one skilled in the art to perform the aforementioned functions as well as other functions that may be desired by the physician.

While the unit is operating, data display 148 will display information concerning the current basal and bolus settings, total drug amount delivery, time or dosage remaining or other information determined to be needed such as battery charge level and the like. After the device has been programmed, it can be inserted into a belt clip 162 of the character shown in FIG. 4 and then attached to the user's belt.

Sensor 157 can take various forms and, for example, can be a glucose sensor for continuous monitoring of blood glucose levels. Such sensors are commercially available and may comprise chemical, electrochemical and optical type sensors. The sensor is operably associated with the delivery device in a manner to provide closed loop control of blood glucose levels. Particularly attractive for monitoring of blood glucose levels is an optical sensor that measures the near-infrared absorption of blood. The sensor is implanted across a vein with readings transmitted via radio waves to a small display unit worn on the patient's wrist. The display unit is, in turn, operably interconnected with the main control unit of the device of the invention in the manner shown in FIG. 22.

Referring to the drawings and particularly to FIGS. 24 through 41, an alternate form of the apparatus of the invention is there shown and generally designated by the numeral 160. This embodiment of the invention, unlike the earlier described embodiments is specially designed to be implanted into the body of the patient. As best seen in FIGS. 24 through 29, the apparatus here comprises a titanium base 162 and a titanium cover 164 that can be joined together by welding at interface 165 to form the hollow, hermetically sealed housing 166 of the device.

Figure 25:
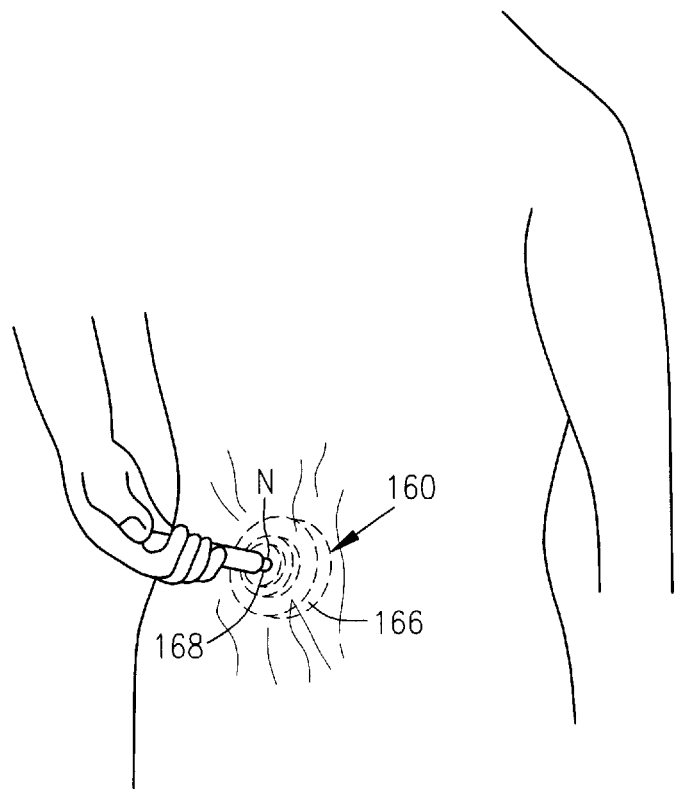
FIG. 25 is a generally perspective, illustrative view showing the delivery device of FIG. 24 implanted within the patient's body and illustrating in the filling of the reservoir of the device using a conventional hypodermic syringe.
Figure 26:
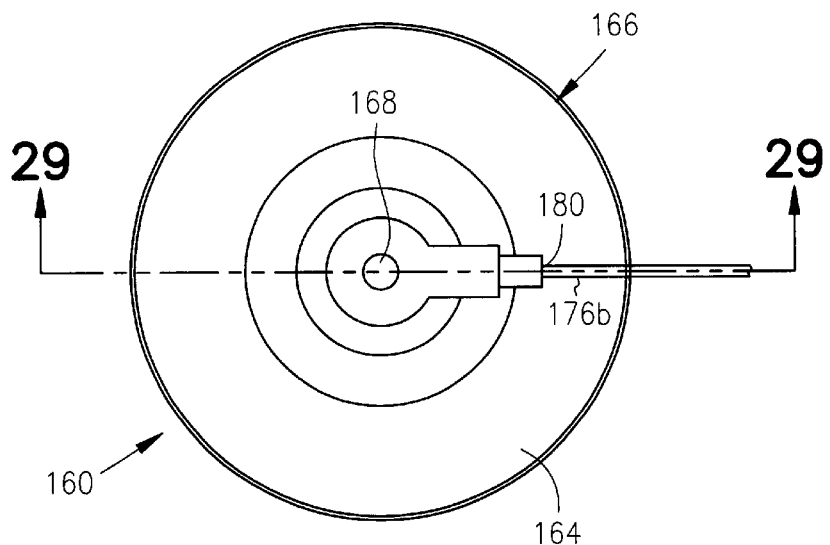
FIG. 26 is a top plan view of the alternate form of fluid delivery apparatus of the invention shown in FIG. 24.
Figure 27:
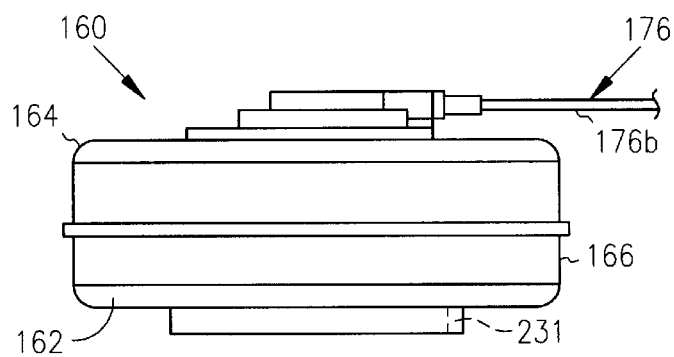
FIG. 27 is a side view of the device shown in FIG. 26.

As shown in FIG. 25, the delivery device of the invention is adapted to be implanted within the patient's body at a location immediately below a layer of skin and includes fill means for filling the device reservoir. The fill means here comprises an access port 168 formed in cover 164 that can be accessed by a hypodermic needle "N". With the arrangement shown in FIGS. 25 and 29, the hypodermic needle can be inserted through the skin to introduce, via the access port, a quantity of liquid medicament such as heparin, morphine, insulin or like medicament through a septum 170, which also forms a part of the fill means, into a medicament reservoir 172. A tapered needle guide 171 disposed within the ullge means of the device supports septum 170 and guides the entry of the hypodermic needle toward reservoir 172 (FIG. 30).

Figure 31:
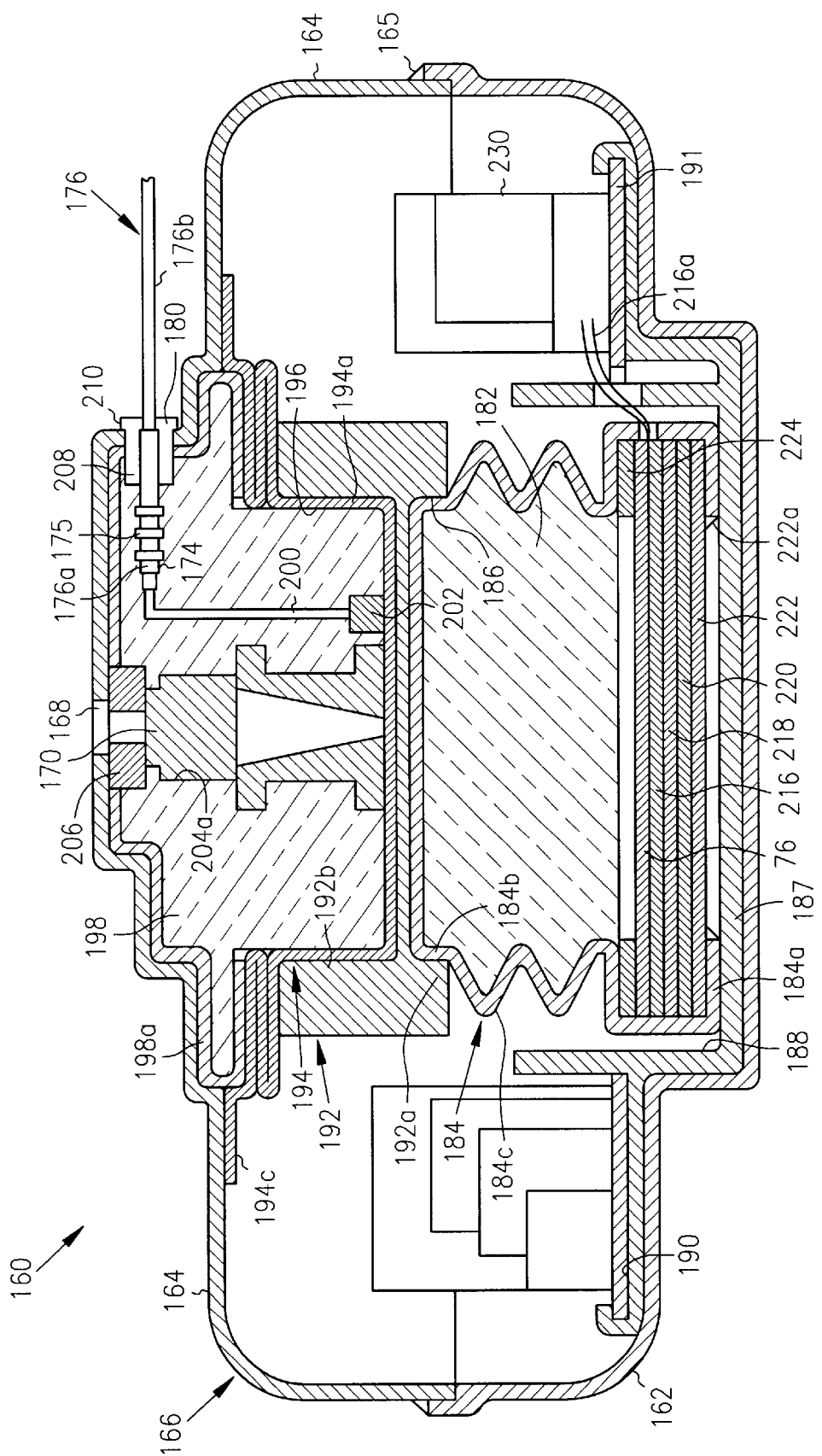
FIG. 31 is a cross-sectional view similar to FIG. 30, but showing the expandable gel in an expanded configuration following delivery of all of the medicament to the patient.
Figure 32:
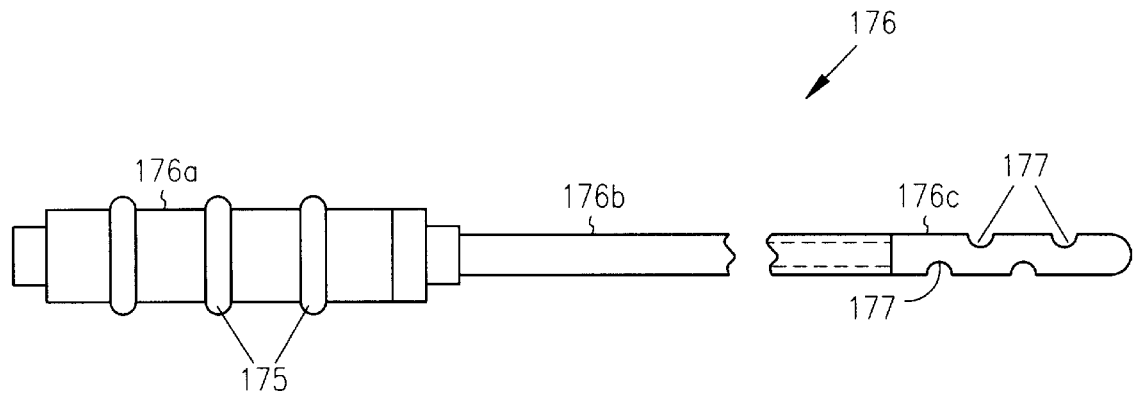
FIG. 32 is a generally perspective, top view of the cannula assembly of the apparatus shown in FIG. 24.
Figure 33:
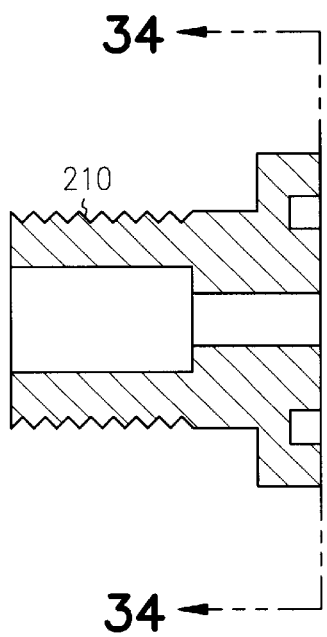
FIG. 33 is a cross-sectional view of the cannula closure member that secures the cannula assembly in position relative to the outlet port of the apparatus.
Figure 34:
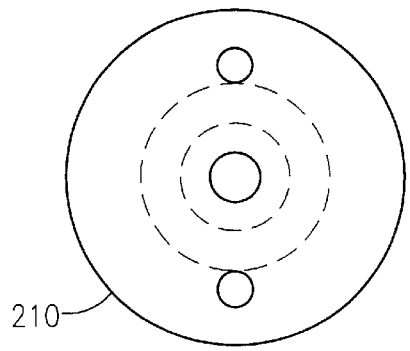
FIG. 34 is a view taken along lines 34—34 of FIG. 33.

During operation, the medicament is delivered from the delivery device via a cannula port 174 to which a cannula assembly 176 can be attached (FIG. 31). Cannula assembly 176 is strategically positioned at the time of implant to deliver the medicament to a selected therapeutic site within the patient's body by means of a suitable porous tip cannula, the character of which will presently be described.

Figure 29:
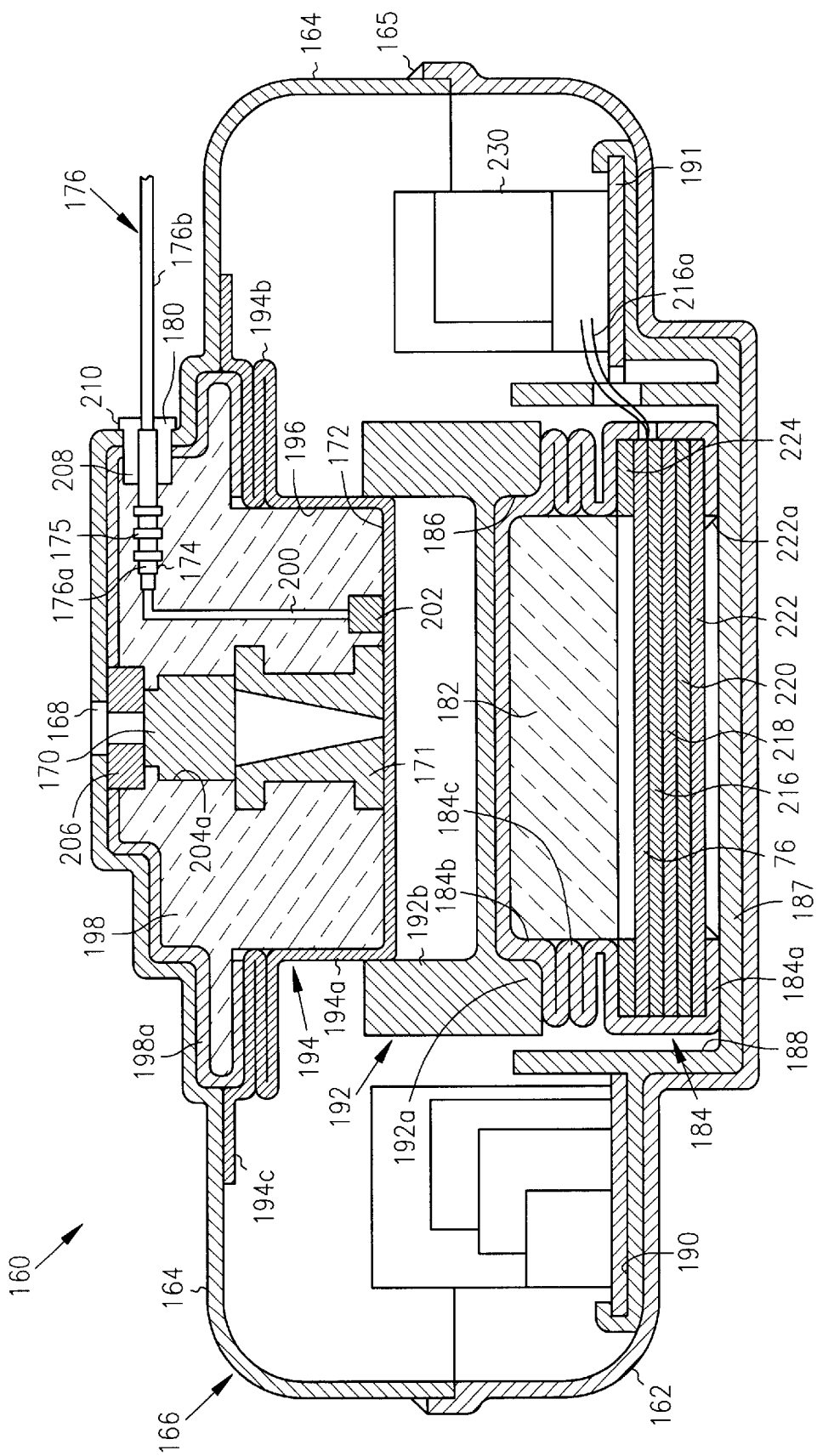
FIG. 29 is an enlarged, cross-sectional view taken along lines 29—29 of FIG. 26.
Figure 30:
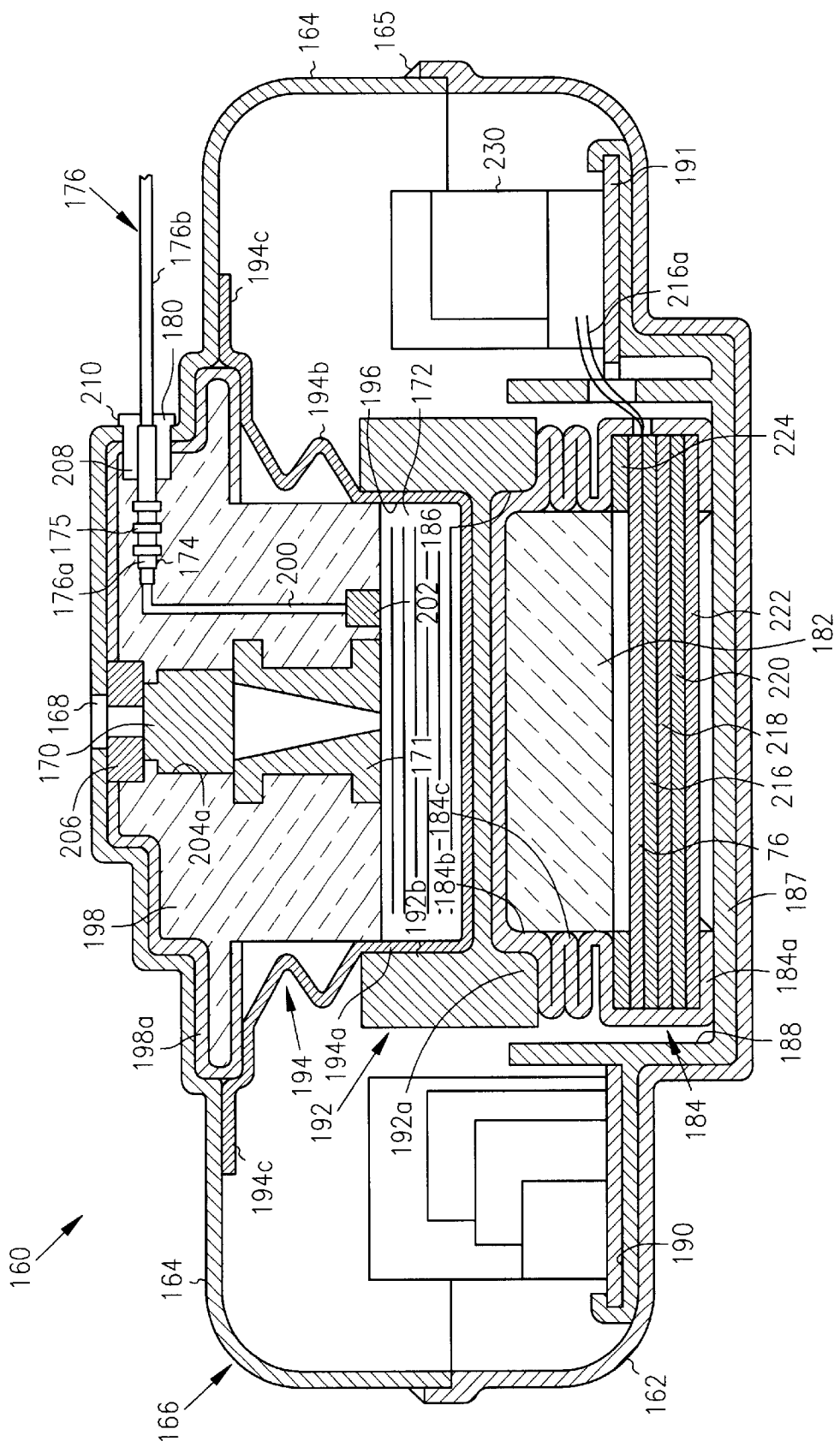
FIG. 30 is a cross-sectional view similar to FIG. 29, but showing the reservoir in a filled condition.

Housing 166 houses the novel light activated stored energy source of the invention which functions to cause the fluids contained within the sealed reservoir 172 of the device, the character of which will presently be described, to flow outwardly thereof through outlet port 180 formed in cover 164 (FIG. 29). As in the earlier described embodiments, the light activated means or stored energy source is provided in the form of a light activated expandable polymer mass 182 which is disposed within an expandable, hermetically sealed metal bellows assembly 184 that is mounted within housing 166 in the manner best seen in FIGS. 29, 30 and 31. Expandable mass 182 can take several forms, but a particularly attractive form for devices of the present invention comprises a semisolid form such as a gel having the attributes of the various expandable gels previously described herein.

Figure 35:
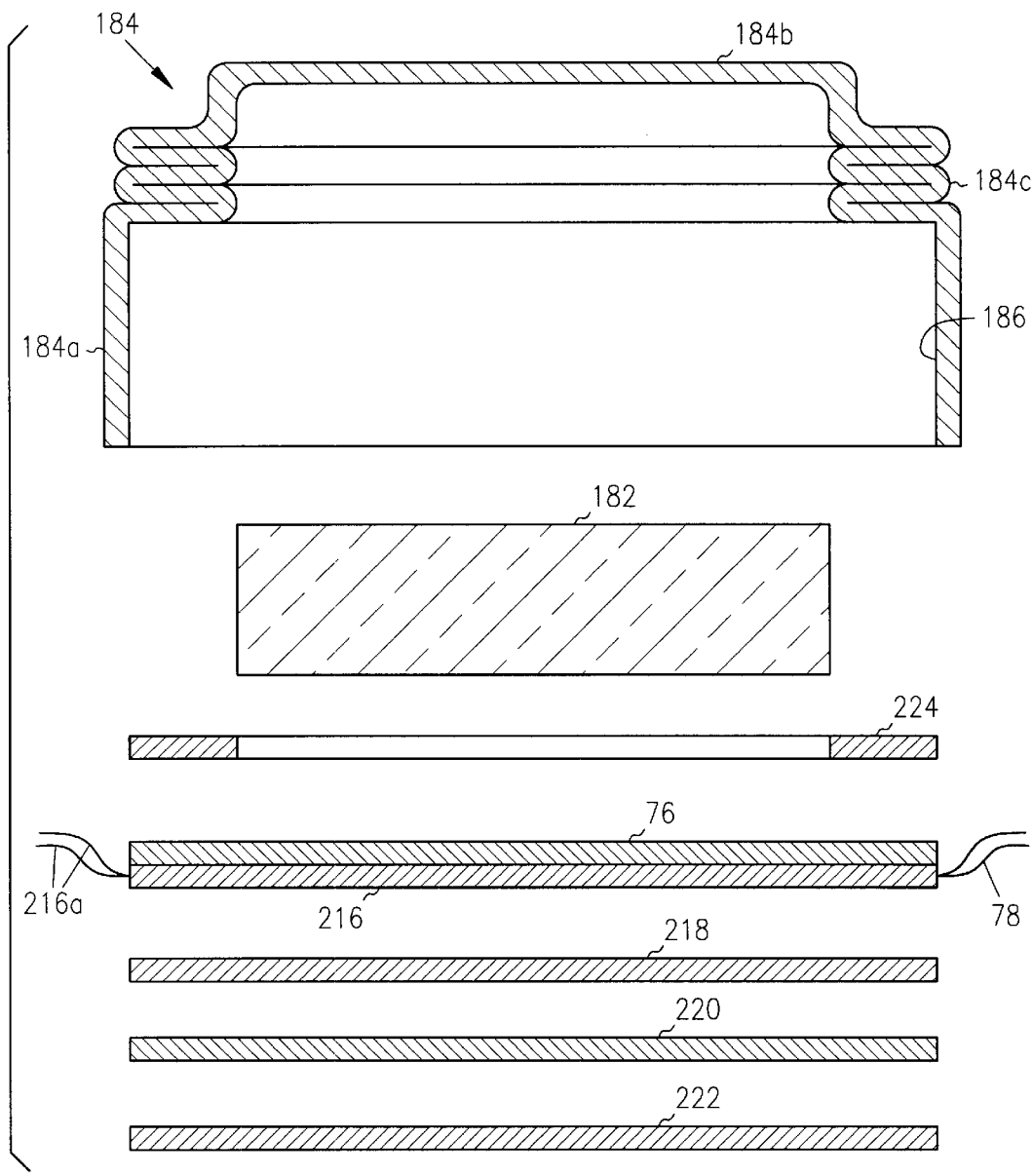
FIG. 35 is a cross-sectional, exploded view of the bellows assembly that houses the expandable gel, the light source and 4X the heater element of the apparatus.
Figures 36, 37:
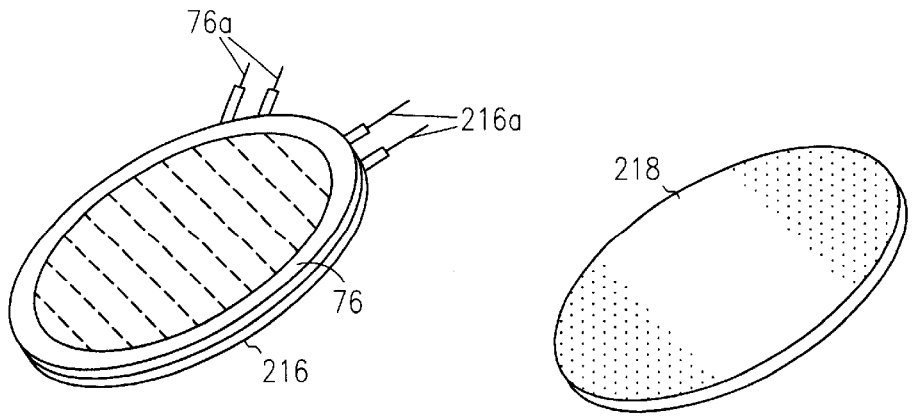
FIG. 36 is a generally perspective view of the light source and foil heater element assembly of the apparatus of the invention.
FIG. 37 is a generally perspective view of the ceramic heat deflector of the apparatus of the invention.

As best seen in FIGS. 29 and 35, bellows assembly 184 includes a base portion 184a, an upstanding, reduced diameter cover 184b and an expandable bellows-like sidewall 184c which are interconnected to define the gel receiving chamber 186. Bellows assembly 184 is closely received within a receiving chamber 188 formed in a carrier assembly 187, which is, in turn, received within base 162.

Figure 38:
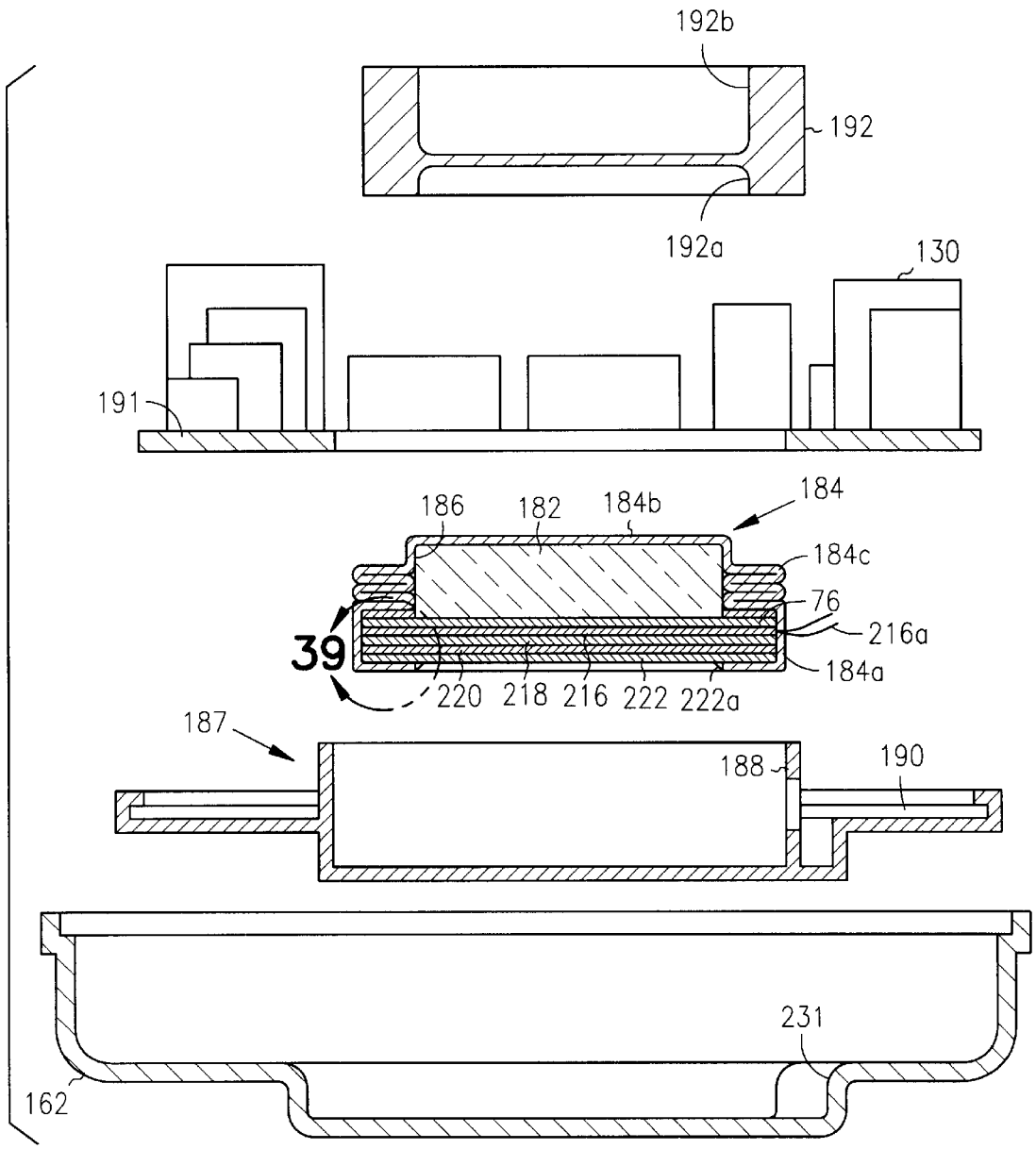
FIG. 38 is an exploded, cross-sectional view of the lower half shell of the apparatus that houses the carrier assembly, the connector ring, the bellows assembly, the expandable gel, the light source, the heating element and the electronics associated therewith.

As illustrated in FIG. 38, surrounding chamber 188 is an electronics receiving channel 190 that supports an annular shaped, printed circuit (PC) board 191 and the electronic components associated therewith, the character of which will presently be described. Upstanding cover 184b of bellows assembly 184 is closely received within the lower portion 192a of a generally annular shaped capture ring 192 (FIGS. 29 and 38) that is disposed intermediate base 162 and cover 164 of housing 166.

As best seen in FIG. 30, the base portion 194a of the upper reservoir assembly 194 of the apparatus is receivable within the upper portion 192b of the capture ring 192. Connected to base portion 194a is a bellows-like wall 194b which cooperates with base portion 194a to form the expandable fluid reservoir 172 of the apparatus. Connected to wall 194b is a connector flange 194c that can be sealably interconnected with the lower surface of cover 164 to form a hermetically sealed chamber 196 a portion of which comprises medicament reservoir 172 (see FIGS. 29 and 30).

Figure 40:
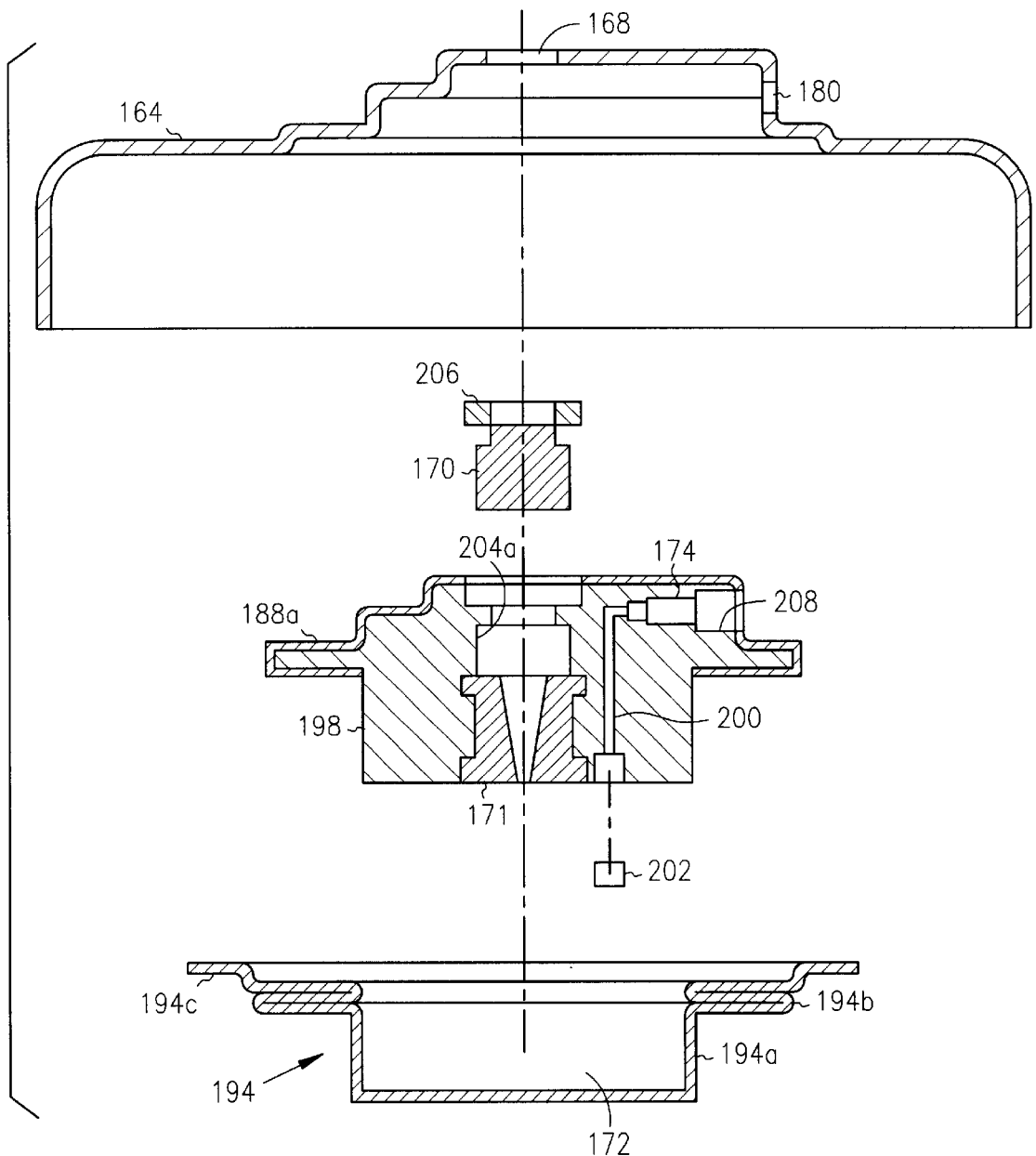
FIG. 40 is an exploded, cross-sectional view of the upper half shell of the apparatus that houses the upper reservoir bellows, the ullage and the spetum assembly.

Disposed within chamber 196 is a novel comolded plastic ullage assembly 198 which includes a fluid passageway 200 that is in communication with reservoir 172 via an impedance frit 202 and with cannula port 174. Formed within ullage assembly 198 proximate needle guide 171 is a septum receiving chamber 204a that houses a septum 170 that is pierceable by the needle "N" of the hypodermic syringe used to fill reservoir 172. Ullage 198 is partially encapsulated within an elastomer 198a. Septum 170 is accessible through sealing ring 206 that engages cover 164 (FIG. 40). Also formed within ullage assembly 198 is an internally threaded cannula connector portion 208 to which the delivery cannula assembly 176 of the apparatus can be sealably interconnected. As best seen by referring to FIG. 31, cannula assembly 176 comprises an elastomeric molded connector portion 176a that is provided with a plurality of spaced apart, rib-like protuberances 175. Connected to connector portion 176a is a hollow cannula 176b and that includes a porous tip 176c that permits fluid to flow outwardly through small outlet passageways 177 formed in the porous tip 176c. Connector portion 176a is sealably receivable within the internally ribbed connector port 174. As best seen in FIG. 31, a threaded cannula closure member 210 (FIGS. 33 and 34), which is threadably receivable within a threaded connector port 208 formed in ullage 198 functions to hold the cannula assembly in position and to compress connector portion 176a in a manner to insure maintenance of a leak tight seal between the cannula assembly and the device housing.

Considering next the novel activating means of the invention for activating gel 182, this means is similar in many respects to the activating means previously described and like numerals are used to identify like components. As before, the light activating means here comprises a light sheet 76 that is carried within a bellows assembly 184. Power is supplied to the light sheet through terminals 78 so that when the light sheet is energized, light is distributed across the entire sheet, changing the internal phosphor layer of the light sheet to a light-emitting state causing the light sheet to emit a bright white light over substantially its entire surface.

Surrounding light sheet 76 is a heater means for maintaining the expandable gel 182 within a substantially constant transition temperature zone. This heater means is here provided as a heater foil 216 upon which light sheet 76 rests in the manner shown in FIGS. 29 and 35. Power is supplied to the heater foil through two terminals 216a that are spaced apart and connected to the heater foil in the manner shown in FIGS. 35 and 36. Terminals 76a and 216a are appropriately potted so as to form a hermetic seal relative to bellows 184. When energized the heater disk will heat the expandable gel to a predetermined, substantially constant temperature to enable appropriate expansion thereof upon stimulation by the light source. As before, the temperature to which the gel is heated is, of course, dependent upon the type of gel being used.

Figure 39:
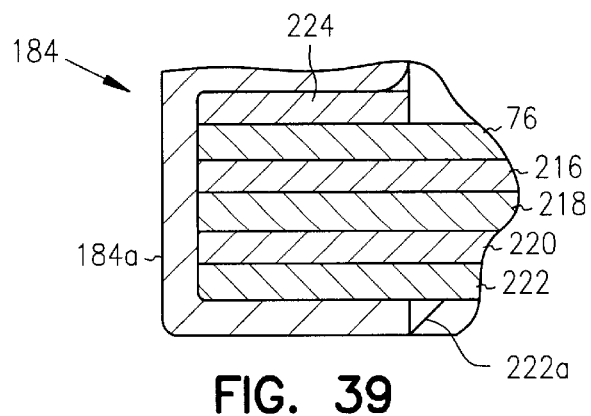
FIG. 39 is a cross-sectional view of the area designated in FIG. 38 by the numeral 39.

The heater foil rests upon a ceramic heat deflector 218 which, in turn, is supported by a silicone seal 220 (FIGS. 29 and 35). Base plate 222 which engages seal 220 functions to hermetically seal chamber 186 as by a weldment 222a (FIG. 39). Circumscribing gel 182 is a ring seal 224 which sealably engages light sheet 76.

Figure 28:
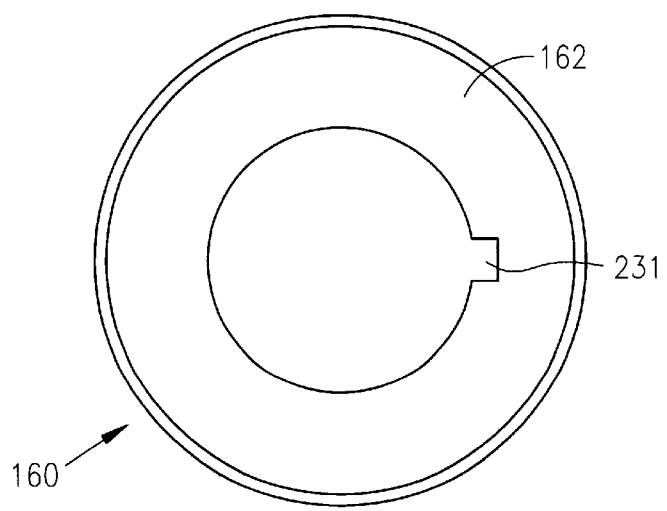
FIG. 28 is a bottom view of the device shown in FIG. 24.

In operation of the apparatus of this latest embodiment of the invention, either before or after the reservoir has been filled in the manner shown in FIG. 30, the electronic controller can be programmed. The electronic controller here includes a microprocessor, a RAM/ROM memory, a power supply, feedback electronic amplifier circuits, timing and control switch matrix circuits and various related circuitry (see FIG. 41). In a manner presently to be described in greater detail, the controller can be programmed to enable the precise delivery of varying dosing volumes in response to either a physiological sensor of the character previously described or to a programmed delivery protocol. The electronic controller can also be programmed to indicate function status to the user. The wiring leading to the electronics 230 is introduced through the electronic lead cavity 231 formed in base 162 (FIG. 28).

Figure 41:
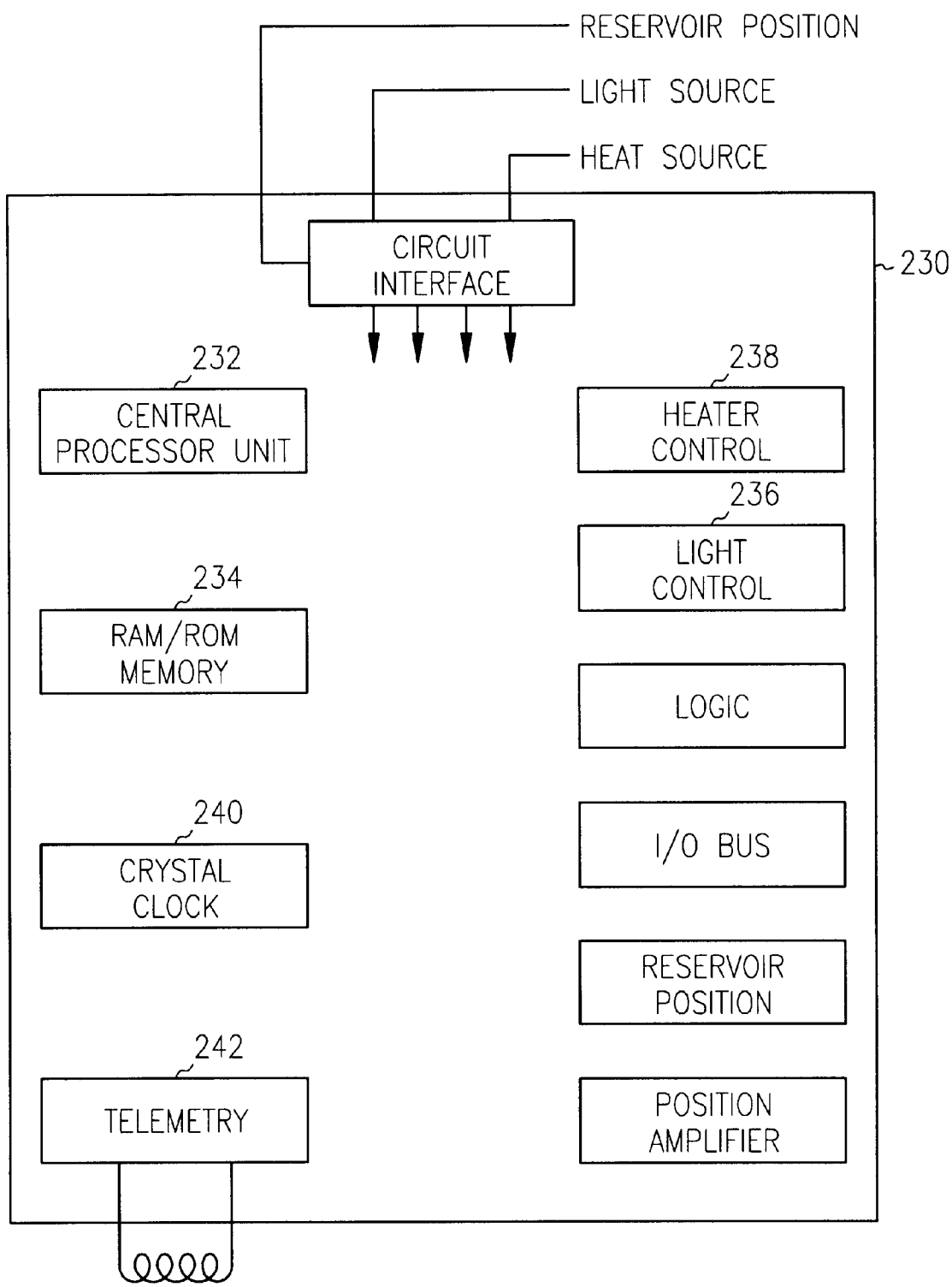
FIG. 41 is a generally diagrammatic view showing the relationship among the various components of the controller and stimulation means of the embodiment shown in FIG. 24.
Figure 42:
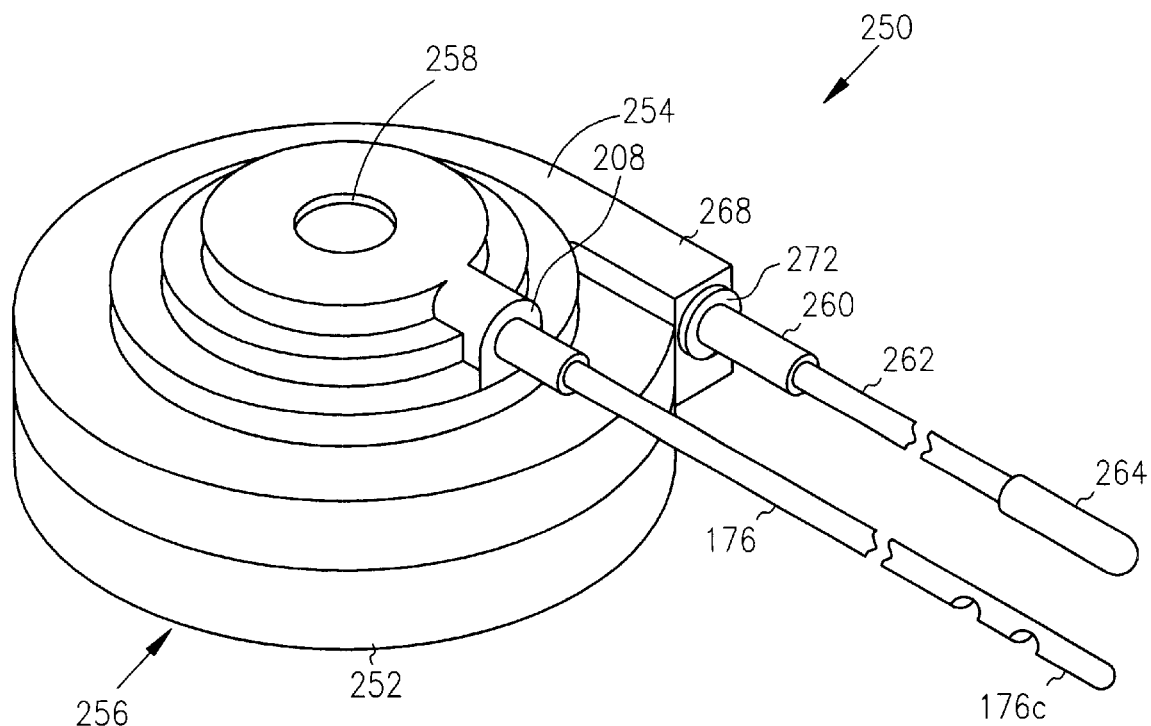
FIG. 42 is a generally perspective view of yet another form of the fluid delivery apparatus of the invention that is implantable within the patient's body.
Figure 43:
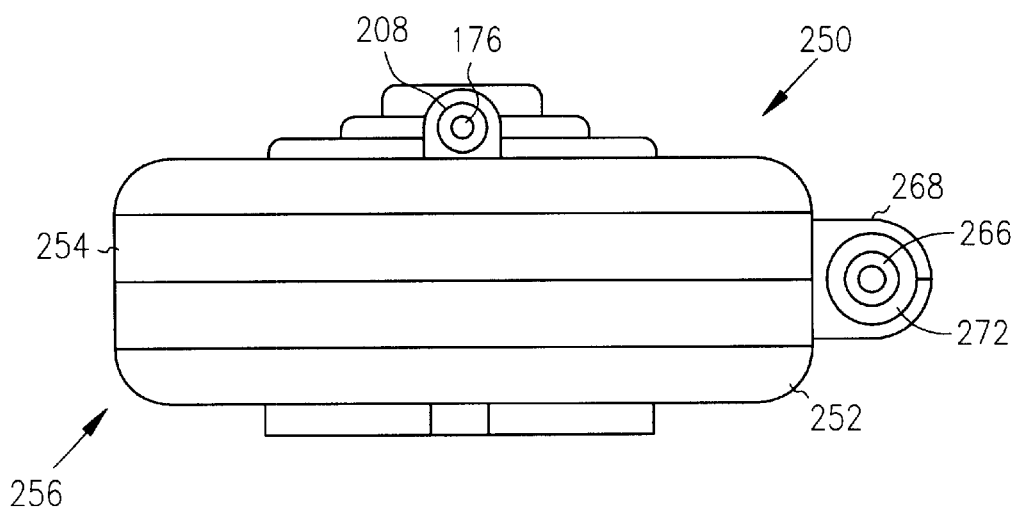
FIG. 43 is a side-elevational view of the apparatus shown in FIG. 42.
Figure 44:
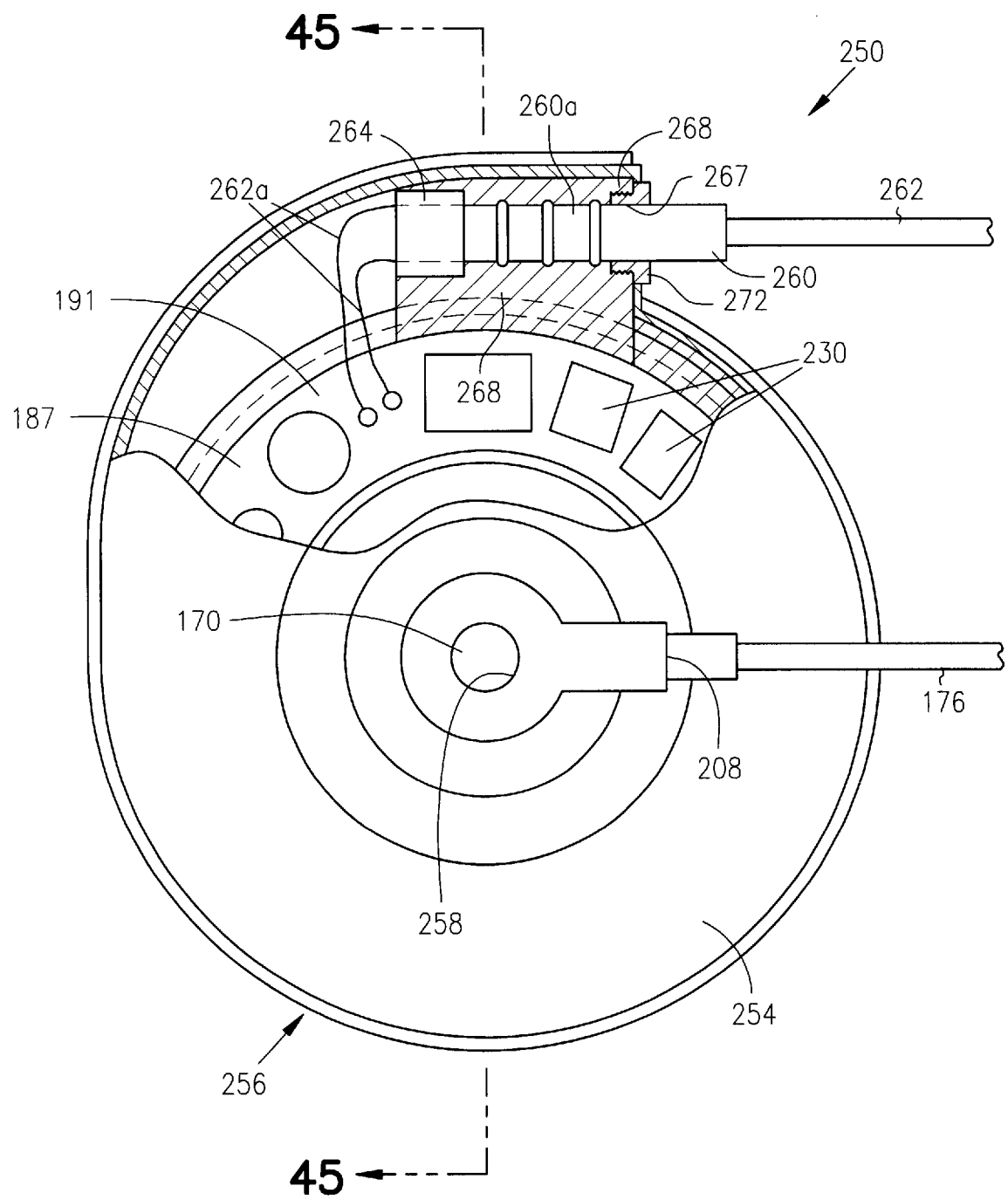
FIG. 44 is a top plan view partly broken away to show internal construction of the apparatus of the shown in FIG. 42.

The electronic controller is similar in many respects to that previously described and as illustrated in FIG. 22. More particularly, as shown in FIG. 41 the electronic controller comprises a central processing unit 232 having a memory 234 and a conventional power source such as a commercially available magnesium oxide or lithium battery. Also forming a part of the electronic controller is a light control 236, a heater control 238, a crystal clock 240 and appropriate telemetry 242. Upon filling the drug reservoir and after the electronic controller is initially programmed in a manner well understood by those skilled in the art, the device can be implanted into the patient. In the paragraphs that follow, the electronics as well as the method of programming the electronics will be further described.

In certain cases, the expandable gel is of a character that the body heat of the patient will maintain the gel at a correct temperature for appropriate activation by the light source. In these instances, it is not necessary to include the means for heating the gel. In other instances, where a temperature in excess of body heat is required to maintain the gel in an appropriate reactive condition, the heater means, or heater foil 216, is included in the apparatus. In this way, the expandable gel can be maintained at an appropriate temperature so that energization of the light source, or light sheet 76, will photo initiate the gel polymerization causing it to expand from the configuration shown in FIG. 30 to the configuration shown in FIG. 31 where the fluid contained within reservoir 172 will be controllably expelled from the device via the cannula assembly 176.

At any time during the fluid delivery step, the light source can be deenergized and the expandable gel 182 will return to the less swollen configuration shown in FIG. 30. With the apparatus in the configuration shown in FIG. 30, additional fluid can be introduced into reservoir 172 in the manner previously described via septum 170 so that the apparatus will assume the configuration shown in FIG. 30. Upon the re-energization of the light source, the expandable gel will once again expand into the configuration shown in FIG. 31 causing fluid to be expelled from the device via cannula assembly 176.

Referring next to FIGS. 42 through 48, still another form of the apparatus of the invention is there shown and generally designated by the numeral 250. This embodiment of the invention is similar in many respects to the embodiment shown in FIGS. 24 through 41 and like numerals are used in FIGS. 42 through 48 to identify like components. This latest embodiment is also designed to be implanted into the body of the patient in the manner previously described. As before the apparatus comprises a titanium base 252 and a titanium cover 254 that can be joined together by welding to form the hollow housing 256 of the device. Unlike the embodiment of the invention shown in FIGS. 24 through 41, here the device uniquely includes integral, interactive sensor means and sensor connecting means for interconnecting the sensor with the device electronics disposed within housing 256.

The delivery device is adapted to be implanted within the patient's body at a location immediately below a layer of skin so that an access port 258 formed in the housing can be accessed by a hypodermic needle to introduce, in the manner previously described, a quantity of liquid medicament such as heparin, morphine, insulin or like medicament through a septum 170 into a drug reservoir. During operation, the medicament is delivered from the delivery device via a cannula port 208 to which a cannula assembly 176 is attached.

Housing 256 houses the novel light activated stored energy source of the invention which functions to cause the fluids contained within the sealed reservoir of the device, the character of which will presently be described, to flow outwardly thereof through an outlet port of the character previously described that is formed in cover 254. As in the earlier described embodiments, the light activated means, or stored energy source, is provided in the form of a light activated expandable polymer mass 182 which is disposed within an expandable, hermetically sealed metal bellows assembly 184 that is mounted within housing 256 in the manner best seen in FIG. 45. Expandable mass 182 is of the same character as previously described herein, as is the bellows assembly 184. Bellows assembly 184 is closely received within a receiving chamber 188 formed within a carrier assembly 187. Surrounding chamber 188 is an electronics receiving channel 189 that supports an annular shaped PC board 191 and the electronic components associated therewith, the character of which are shown in FIG. 46 and which have previously been described. Upstanding cover 184b is closely received within the lower portion 192a of a generally annular shaped capture ring 190 that is disposed intermediate base 252 and cover 254 of housing 256.

Figure 45:
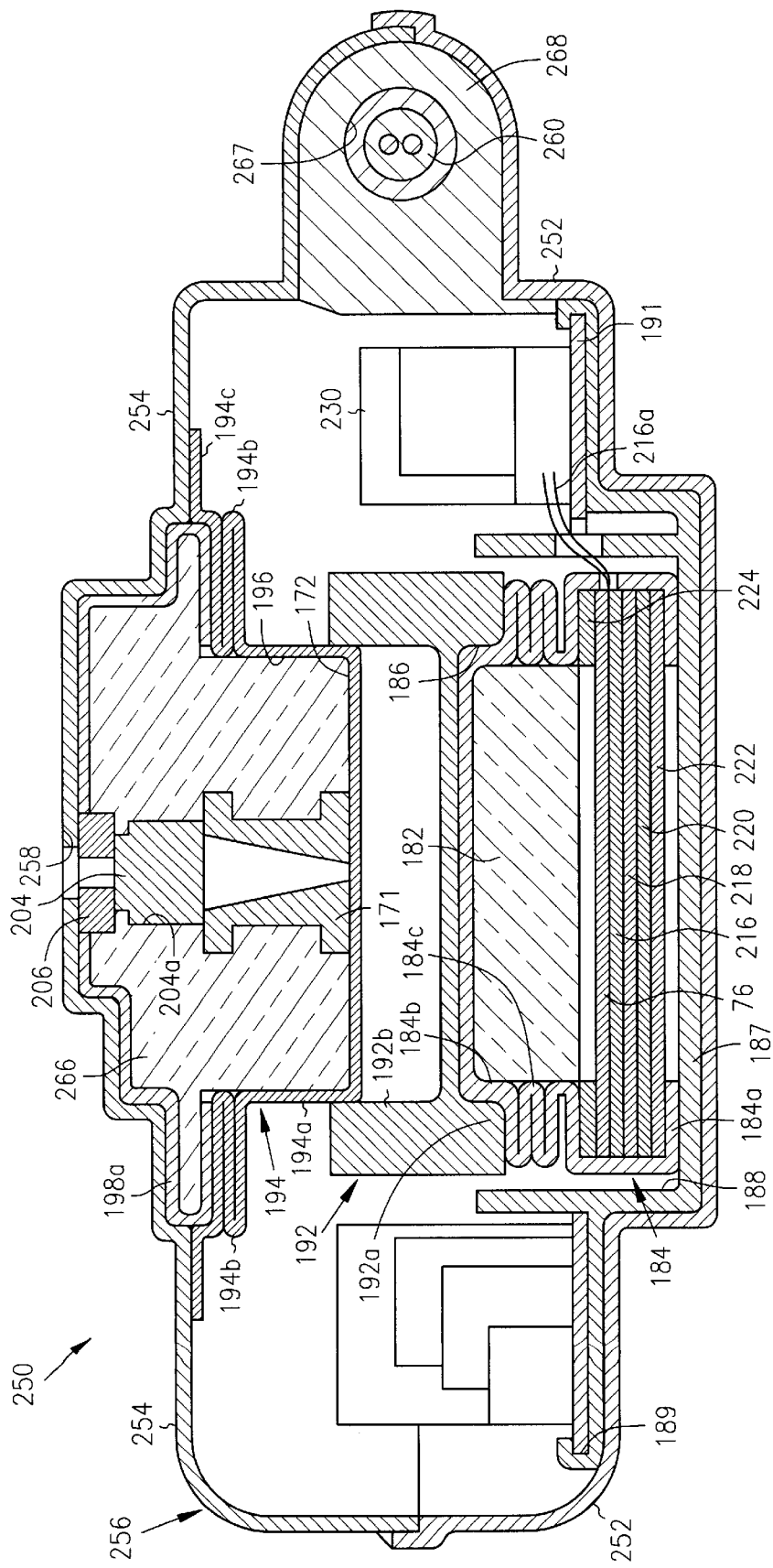
FIG. 45 is a cross-sectional view taken along lines 45—45 of FIG. 44.
Figure 46:
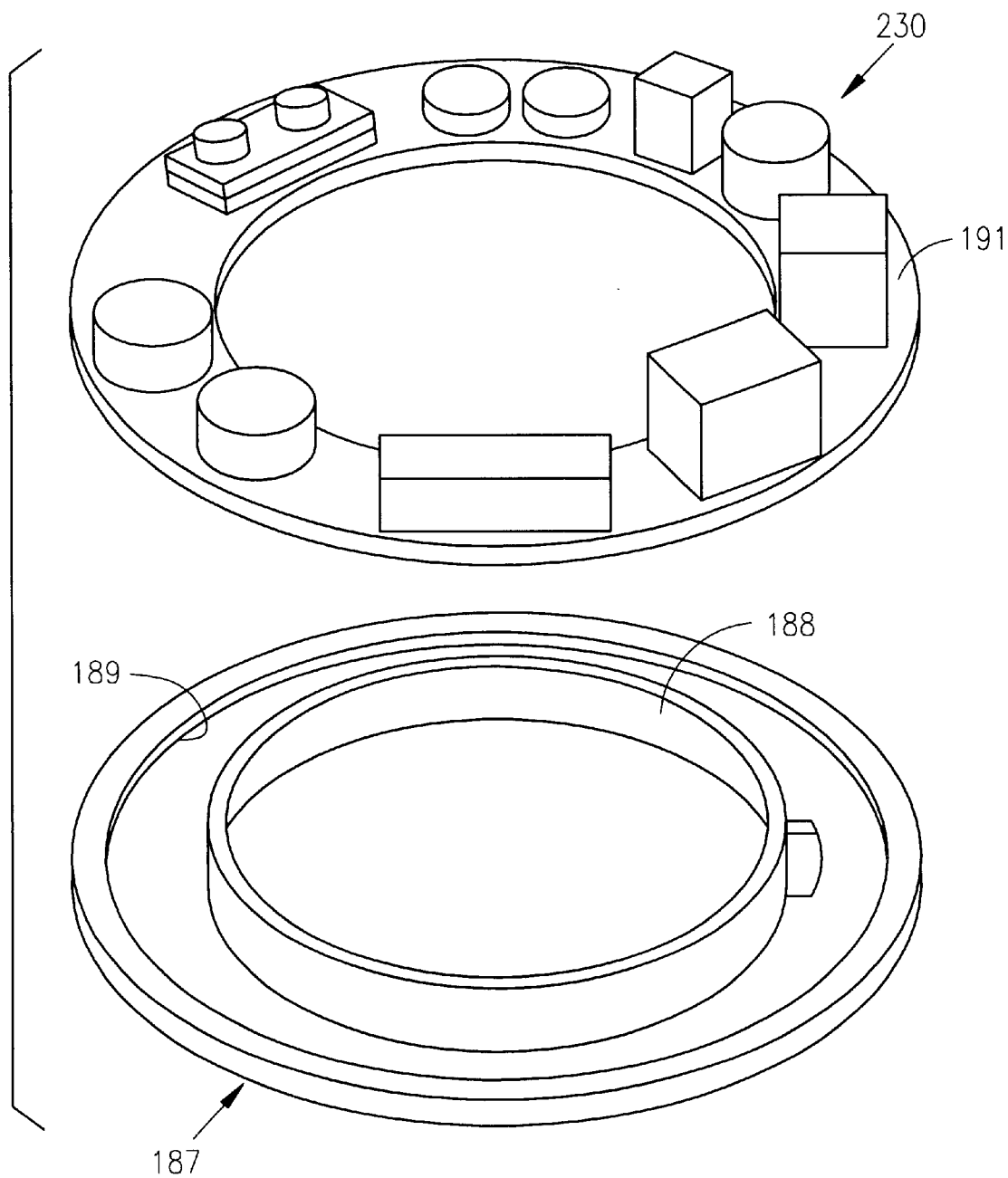
FIG. 46 is a generally perspective, exploded view of the carrier assembly, the printed circuit board, and associated electronics of the apparatus shown in FIG. 42.

As best seen in FIG. 45, the base portion 194a of the reservoir assembly 194 of the apparatus is receivable within the upper portion and 192b of capture ring 192.

Connected to base portion 194a is a bellows-like wall 194b which cooperates with base portion 194a to form the fluid reservoir 172 of the apparatus. Connected to wall 194b is a connector flange 194c that can be sealably interconnected with the lower surface of cover 254 to form a hermetically sealed chamber 196 (see FIG. 45).

Disposed within chamber 196 is an ullage assembly 266 which includes a fluid passageway that is in communication with the fluid reservoir and with a cannula port 208, the construction of which is substantially identical to that previously described herein. Formed within ullage assembly 266 is a septum receiving chamber 204a that houses a septum 170 that is pierceable by the needle of the hypodermic syringe used to fill the fluid reservoir. Septum 204 is accessible through a septal port 258 formed in cover 254.

Also formed within ullage assembly 266 is the previously identified cannula connector port 208 to which the delivery cannula assembly 176 of the apparatus can be sealably interconnected in the manner previously described.

Connected to and extending from cover 254 is the previously identified sensor means of the invention, for sensing various body conditions. As before, the sensor means, which may comprise commercially available chemical, electorchemical, and optical type sensors, here includes a connector 260, a conduit 262 and a sensor 264. Connector 260 includes a ribbed body portion 260a that is sealably receivable within a threaded receiving opening 267 formed in a protuberance 268 that extends from the periphery of housing 256 in the manner shown in FIGS. 42 and 44. Conduit 262 extends through connector 260 and includes connector leads 262a that are connected to PC board 191 in the manner best seen in FIG. 64, A threaded connector 272, which is threadably received within threaded receiving t opening 267 formed in protuberance 268, maintains sensor connector 260 securely in position. The sensor tip 264 is appropriately positioned within the patient at the time of implantation of the delivery device.

Figure 47:
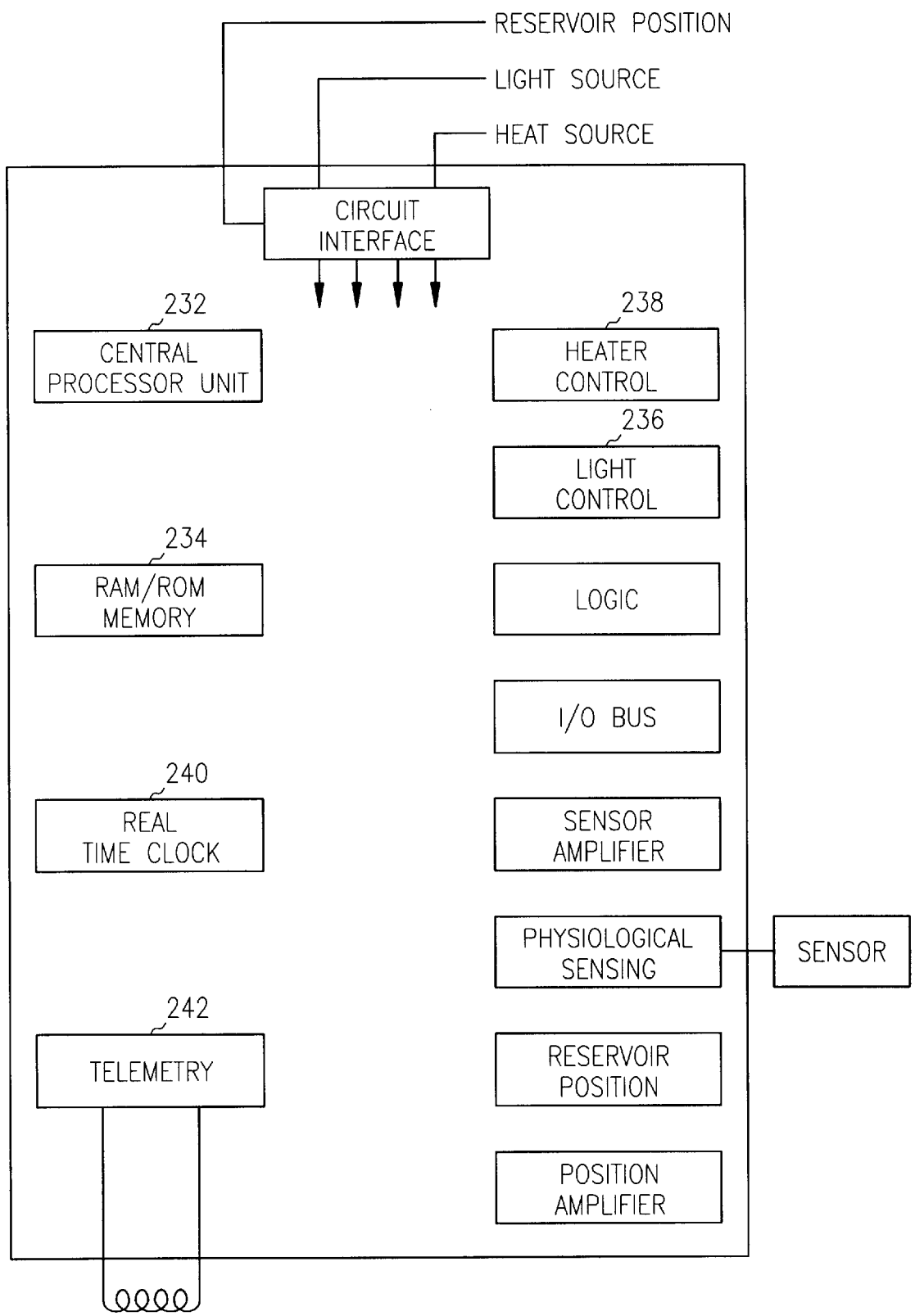
FIG. 47 is a generally diagrammatic view showing the relationship among the various components of the controller and stimulation means of the embodiment shown in FIG. 42.
Figure 48A:
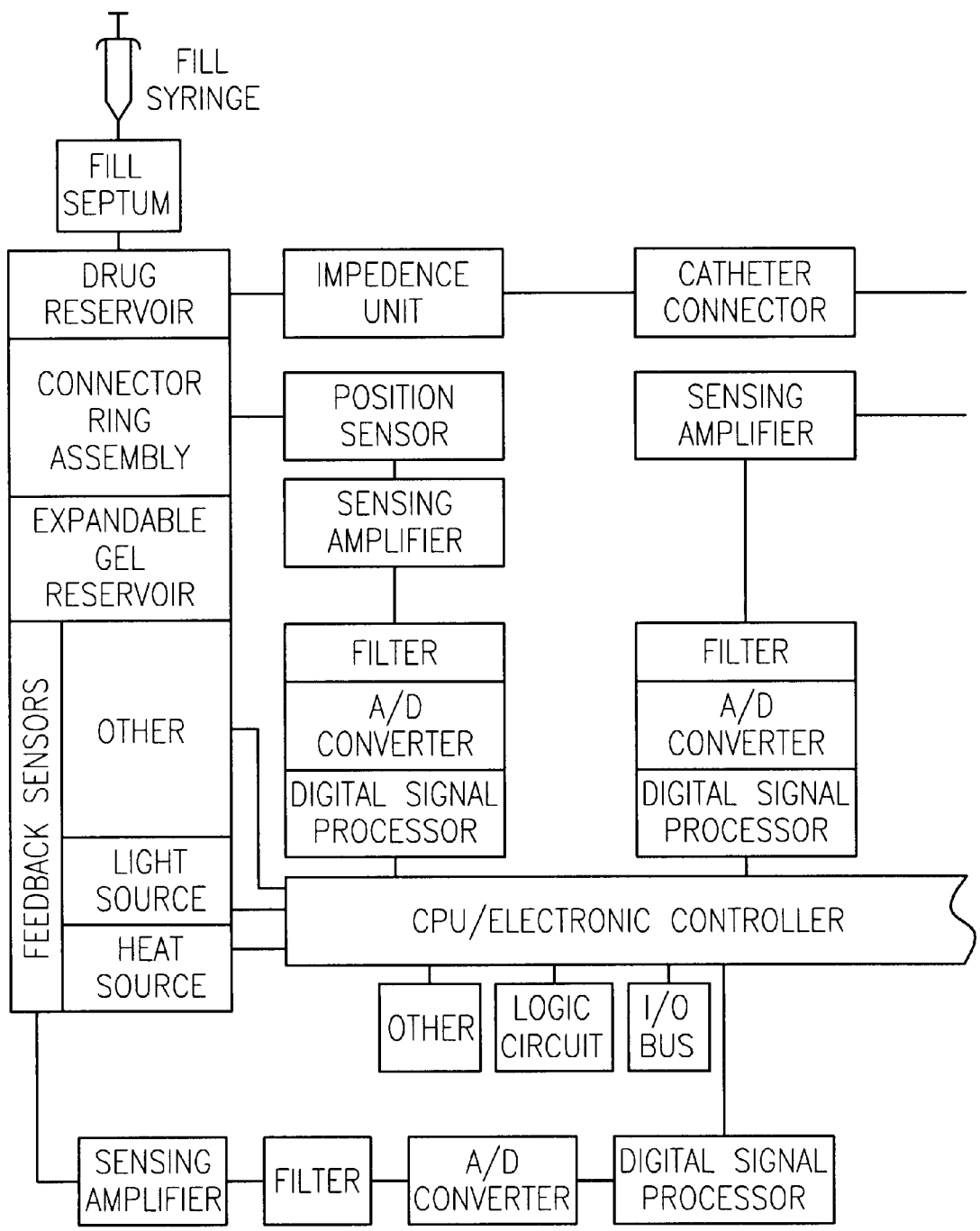
FIGS. 48A and 48B when considered together comprise a generally diagrammatic view further illustrating the relationship among the major operating components of the apparatus including an implantable physiological sensor, system telemetry and external programming capability.
Figure 48B:
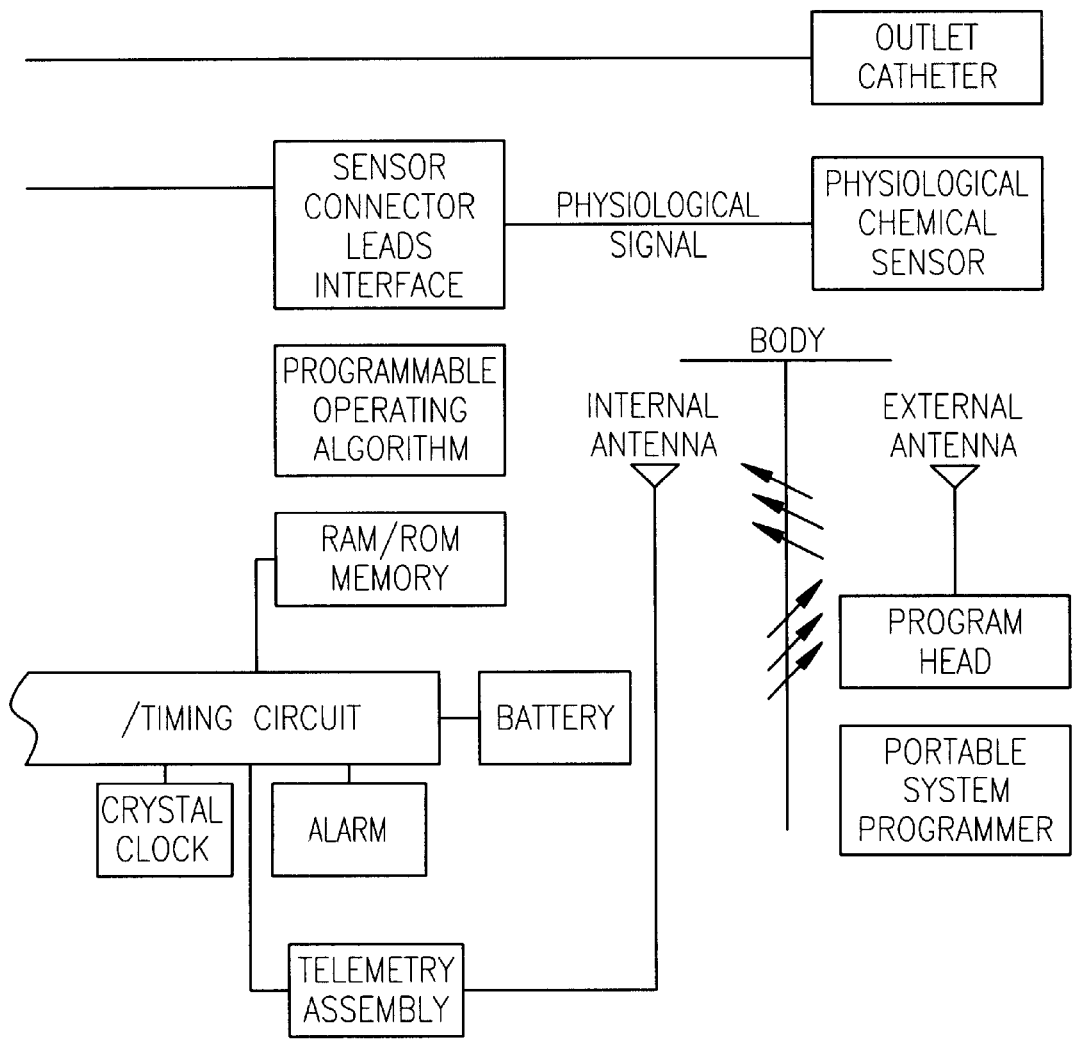

Turning to FIGS. 47 and 48, it can be seen that the electronic controller of this embodiment is similar in many respects to that previously described and as illustrated in FIG. 41. More particularly, as shown in FIG. 47 the electronic controller here comprises a central processing unit 232 having a memory 234 and a conventional power source such as a battery as well as the various components described in connection with the last embodiment. Also forming a part of the electronic controller is a light control 236, a heater control 238, a crystal real time clock 240 and appropriate telemetry 242 (see FIG. 47). Further details relating to the electronic controller and its relationship with the operating components of the delivery device are shown in block diagram form in FIG. 48. More particularly, this figure shows the relative relationship among the fill means of the device, the fluid reservoir, the device gel reservoir, the light source, the heat source, the catheter and the programmable sensor. Additionally, FIG. 48 illustrates, in block diagram form, the relationship among these components and the various components that make up the electronics of the device including the central processing unit, the RAM/ROM memory, the digital signal processor, the logic circuit, and the telemetry assembly. As previously mentioned, the various electronic components of the device are well known to those skilled in the art and their interconnection and programming to meet the various requirements of the physician are well within the capability of the skilled artesan.

As indicated in FIG. 48, this latest embodiment of the invention uniquely comprises an in vivo, physiological sensing portion that is capable of detecting and responding to the physiological, physiochemical, chemical, optical and electronic changes in the body or bloodstream. The physiological sensing portion and its sensing structure may comprise an electronic, chemical or optical interface designed to measure specific parameters or changes in parameters and to compare known values combined within the associated delivery system electronic memory. It will be clear to those skilled in the art that when the physiological sensing portion is coupled directly or indirectly with a sensing amplifier, with related filter, analog to digital convertor, signal processor and other sensing circuitry operating in conjunction with the programmable system electronics/CPU that various physiological chemical changes maybe sampled and compared with known parameters set forth in a look-up table carried in device memory.

When necessary the CPU/electronic controller can be programmed to execute a command function signal to initiate control and/or terminate the timed operation and frequency of light activation, pulse width duration and, when necessary, associated temperature circuitry. The resulting process is responsive to the physiological/chemical sensor circuitry and the output can be converted to digital signals and referenced against other controlling data will provide the interactive operating mode of operation of the delivery system.

Other sensors and related sensing circuitry, which comprise a part of the electronics 230 of the apparatus, will also provide light source and temperature confirming on/off function feedback signals for associated pulse logic sequences as well as position indication of the bellows connector ring assembly. Additionally, drug volume displacement, delivery rate over time measurements, battery life and system temperature and like data can be provided. Other alarm data can also be provided as, for example, reservoir condition and component malfunction. The telemetry assembly relies on the use of a radio frequency transmission system that is commercially available and well known to those skilled in the art. With the use of such a system, it is possible to up link the system performance, event history data residing in the receiving register and other operating perameters and current values such as the remaining drug volume and battery life.

Further the telemetry assembly can receive down link instructions upon proper interrogation and address confirmation in the programmable system operating mode. Such programming changes of function and operating values can be implemented and recorded within the delivery system electronics controller memory. This program can also be accomplished through the use of an operably associated portable system programmer and programming head which is also commercially available and well known to those skilled in the art.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device for use in infusing medicinal fluid into a patient at a controlled rate comprising:
    (a) a housing having a surface and including a base and a cover superimposed over said base;
    (b) means for forming, in conjunction with said surface of said housing, a fluid reservoir containing a fluid and having an inlet and an outlet;
    (c) a light stimulated, expandable means disposed within said housing in proximity to said reservoir, said expandable means comprising a semi-solid, which, upon being stimulated, will act upon said fluid within said reservoir to cause said fluid to flow outwardly of said outlet of said reservoir;
    (d) stimulation means for stimulating said expandable means, said stimulation means comprising a source of light; and
    (e) infusion means in communication with said outlet of said reservoir for infusing fluid from said fluid reservoir into the patient.

2. The device as defined in claim 1 in which said expandable means is disposed within an expandable bellows disposed within said housing.

3. The device as defined in claim 1 in which said infusion means comprises a hollow cannula connected to, but spaced apart from said housing.

4. The device as defined in claim 1 in which said expandable means comprises a gel.

5. The device as defined in claim 1 in which said stimulation means comprises a light sheet operably associated with said expandable means.

6. The device as defined in claim 1 further including fill means for filling said reservoir.

7. The device as defined in claim 1 in which said base and said cover are releasably interconnected.

8. The device as defined in claim 1 further including heater means disposed proximate said expandable means for heating said expandable means.

9. The device as defined in claim 1 in which said means for forming said reservoir comprises a distendable membrane and in which said device further includes a pusher member disposed within said housing for acting upon said distendable membrane upon expansion of said expandable means.

10. The device as defined in claim 9 in which said pusher member is generally dome shaped and is disposed within said housing.

11. A device for use in infusing medicinal fluid into a patient at a controlled rate comprising:
    (a) a housing having a surface and including a base and a cover superimposed over said base;
    (b) distendable means for forming, in conjunction with said surface of said housing, a fluid reservoir having an inlet and an outlet, said distendable means comprising at least one distendable membrane at least a portion of which is movable within said housing from a first position to a second position;
    (c) expandable means disposed within said housing in proximity to said distendable membrane, said expandable means comprising a semi-solid, which, upon being exposed to light, will cause said distendable membrane to move toward said second position to cause fluid within said reservoir to flow outwardly of said outlet of said reservoir;
    (d) a source of light for stimulating said expandable means, said source of light comprising a light sheet;
    (e) infusion means in communication with said outlet of said reservoir for infusing fluid from said fluid reservoir into the patient; and
    (f) fill means for filling said reservoir.

12. The device as defined in claim 11 in which said infusion means comprises a hollow cannula.

13. The device as defined in claim 11 in which said expandable means comprises a gel.

14. The device as defined in claim 11 further including heater media for heating said expandable means, said heater means comprising a heater coil circumscribing said source of light.

15. The device as defined in claim 11 in which said cover includes a cavity and in which said distendable membrane is sealably connected to said cover and spans said cavity.

16. The device as defined in claim 15 further including pusher means disposed within said housing proximate said distendable membrane.

17. The device as defined in claim 16 in which said expandable means is disposed within an expandable bellows disposed within said housing.

18. A device for use in infusing medicinal fluid into a patient at a controlled rate comprising:
   (a) a housing having a surface and including a base and a cover superimposed over said base, said cover having a cavity defining an internal surface;
   (b) distendable means for forming, in conjunction with said internal surface, a fluid reservoir having an inlet and an outlet, said distendable means comprising at least one distendable membrane at least a portion of which is movable within said housing from a first position spaced apart from said internal surface to a second position proximate said internal surface;
   (c) fill means for filling said fluid reservoir;
   (d) expandable means disposed within said housing, said expandable means comprising a gel which, upon being stimulated, will cause said distendable membrane to move toward said second position to cause fluid within said reservoir to flow outwardly of said outlet of said reservoir;
   (e) stimulation means for stimulating said gel, said means comprising a light source; and
   (f) infusion means in communication with said outlet of said reservoir for infusing fluid from said fluid reservoir into the patient.

19. The apparatus as defined in claim 18 further including quick connect means for releasably connecting said infusion means to said housing.

20. The apparatus as defined in claim 18 further including flow control means carried by said housing for controlling fluid flow toward said infusion means.

21. The apparatus as defined in claim 18 further including a heater coil disposed proximate said expandable means for controllably heating said expandable means.

22. The apparatus as defined in claim 18 in which said light source comprises a light sheet comprising a flexible electroluminescent film.

23. The apparatus as defined in claim 22 in which said light sheet further includes a light generating phosphor compound.

24. A device for use in infusing medicinal fluid into a patient at a controlled rate comprising:
   (a) a housing having a surface and including a base and a cover superimposed over said base;
   (b) distendable means for forming, in conjunction with said surface of said housing, a fluid reservoir having an inlet and an outlet, said distendable means comprising at least one distendable membrane at least a portion of which is movable within said housing from a first position to a second position;
   (c) expandable means disposed within said housing in proximity to said distendable membrane, said expandable means comprising a semi-solid, which, upon being stimulated by light, will act upon said distendable membrane to move said membrane toward said second position to cause fluid within said reservoir to flow outwardly of said outlet of said reservoir;
   (d) stimulation means for stimulating said expandable means, said stimulation means comprising a light sheet including a flexible electroluminescent film; and
   (e) infusion means in communication with said outlet of said reservoir for infusing fluid from said fluid reservoir into the patient.

25. The device as defined in claim 24 further including controller means operably associated with said stimulation means for controlling said stimulation means.

26. The device as defined in claim 25 in which said stimulation means further comprises a light generating polymer.

27. The device as defined in claim 26 in which said expandable means comprises a gel.

28. The device as defined in claim 27 further including a sensor carried by said patient for sensing a body condition, said sensor being operably associated with said controller means.

29. The device defined in claim 27 further including a glucose sensor carried by the patient for continuous monitoring of the blood glucose level of the patient, said glucose sensor being operably associated with said controller means.

30. An implantable device for implantation within a patient for infusing medicinal fluid into the patient at a controlled rate comprising:
   (a) a housing having a surface and including a base and a cover superimposed over said base;
   (b) means for forming in conjunction with said surface of said housing, a fluid reservoir containing a fluid and having an inlet and an outlet;
   (c) a light stimulated, expandable means disposed within said housing in proximity to said reservoir, said expandable means comprising a semi-solid, which upon being stimulated, will act upon said fluid within said reservoir to cause said fluid to flow outwardly of said outlet of said reservoir; and
   (d) stimulation means for stimulating said expandable means, said stimulation means comprising a source of light.

31. The device as defined in claim 30 in which said expandable means is disposed within an expandable bellows disposed within said housing.

32. The device as defined in claim 30 in which said means for forming said reservoir comprises an expandable bellows.

33. The device as defined in claim 30 in which said expandable means comprises a gel.

34. The device as defined in claim 30 in which said stimulation means comprises a light sheet operably associated with said expandable means.

35. The device as defined in claim 30 further including fill means for filling said reservoir.

36. The device as defined in claim 35 in which said fill means comprises a septum carried by said housing, said septum being pierceable by a cannula inserted into said septum.

* * * * *